(12) United States Patent
Chen et al.

(10) Patent No.: US 12,319,748 B2
(45) Date of Patent: Jun. 3, 2025

(54) ANTIBODY BINDING TO HUMAN HER2 AND PREPARATION METHOD AND USE THEREOF

(71) Applicant: SUNSHINE GUOJIAN PHARMACEUTICAL (SHANGHAI) CO., LTD., Shanghai (CN)

(72) Inventors: Jianhe Chen, Shanghai (CN); Xuesai Zhang, Shanghai (CN); Le Zhao, Shanghai (CN); Fei Xu, Shanghai (CN); Qingrou Li, Shanghai (CN); Haomin Huang, Shanghai (CN); Zhenping Zhu, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 170 days.

(21) Appl. No.: 17/265,143

(22) PCT Filed: Aug. 1, 2019

(86) PCT No.: PCT/CN2019/098793
§ 371 (c)(1),
(2) Date: Feb. 1, 2021

(87) PCT Pub. No.: WO2020/025013
PCT Pub. Date: Feb. 6, 2020

(65) Prior Publication Data
US 2021/0309759 A1    Oct. 7, 2021

(30) Foreign Application Priority Data

Aug. 1, 2018 (CN) .......................... 201810861135.5

(51) Int. Cl.
*C07K 16/32* (2006.01)
*A61K 39/00* (2006.01)
*A61P 35/00* (2006.01)

(52) U.S. Cl.
CPC .............. *C07K 16/32* (2013.01); *A61P 35/00* (2018.01); *A61K 2039/505* (2013.01); *C07K 2317/24* (2013.01); *C07K 2317/34* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| CN | 104530236 A | 4/2015 |
|---|---|---|
| EP | 2719706 A1 | 4/2014 |
| EP | 3466976 A1 | 4/2019 |

OTHER PUBLICATIONS

Meng et al. Oncogenesis. 2016. 5: e211 (Year: 2016).*
Cho et al. Nature. 2003. 421: 756-760 (Year: 2003).*
Edwards et al. J. Mol. Biol. 2003. 334: 103-118. (Year: 2003).*
Lloyd et al. Protein Engineering, Design & Selection. 2009. 22(3): 159â168 (Year: 2009).*
Meyer et al. British Journal of Haematology. 2018. 180: 808â820 (Year: 2018).*
Vajdos et al. J Mol Biol. 2002. 320: 415-428 (Year: 2002).*
UniProt. ERBB2_Human. Retrieved on Jun. 6, 2024 from <URL: https://www.uniprot.org/uniprotkb/P04626/entry> (Year: 2024).*
Fu et al., "Construction, optimization and characterization of novel anti-HER2 antibody for cancer therapy" Medicine and Health Science, 2016, n 1, p. 5, 6, 18-28, 33, 35-41, and 68.
Fisher et al., "Structure of the Complex between HER2 and an Antibody Paratope Formed by Side Chains from Tryptophan and Serine" J. Mol., Biol. 2010, v 402, p. 217-229.
Manijeh et al., "Linear and Conformational B Cell Epitope Prediction of the HER 2 ECD-Subdomain III by in silico Methods" Asian Pacific Journal of Cancer Prevention, 2012, v 13, p. 3053-3059.
Zhou et al., "Initial prediction of human epidermal growth factor receptor-2 B cell epitope" 2010, v 05, abstract and table 4.

* cited by examiner

*Primary Examiner* — Zachary S Skelding
*Assistant Examiner* — Brianna K Swartwout
(74) *Attorney, Agent, or Firm* — Gregory P. Einhorn; Greer, Burns & Crain, Ltd.

(57) ABSTRACT

Provided is an antibody binding to human HER2 or an antigen-binding fragment thereof capable of specifically binding to human HER2. Compared with Perjeta, the combination of the antibody or an antigen-binding fragment thereof and Herceptin has improved biological activity in inhibiting the proliferation of tumor cells overexpressing HER2. The antibody or an antigen-binding fragment thereof has an antigen-binding epitope different from known antibodies binding to human HER2, can be used to prepare a drug for treating a disease related to HER2 overexpression, such as cancer, and has good prospects for clinical application.

18 Claims, 15 Drawing Sheets

Specification includes a Sequence Listing.

IP-SKBR3

```
                            SEQUENCE LISTING

<160> NUMBER OF SEQ ID NOS: 26

<210> SEQ ID NO 1
<211> LENGTH: 652
<212> TYPE: PRT
<213> ORGANISM: Homo sapiens

<400> SEQUENCE: 1

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335
```

```
Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr
                645                 650

<210> SEQ ID NO 2
<211> LENGTH: 1956
<212> TYPE: DNA
<213> ORGANISM: Homo sapiens

<400> SEQUENCE: 2
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
```

-continued

```
attgtgcgag gcacccagct ctttgaggac aactatgccc tggccgtgct agacaatgga      360
gacccgctga acaataccac ccctgtcaca ggggcctccc caggaggcct gcgggagctg      420
cagcttcgaa gcctcacaga gatcttgaaa ggaggggtct tgatccagcg aaaccccag      480
ctctgctacc aggacacgat tttgtggaag gacatcttcc acaagaacaa ccagctggct      540
ctcacactga tagacaccaa ccgctctcgg gcctgccacc cctgttctcc gatgtgtaag      600
ggctcccgct gctggggaga gagttctgag gattgtcaga gcctgacgcg cactgtctgt      660
gccggtggct gtgcccgctg caaggggcca ctgcccactg actgctgcca tgagcagtgt      720
gctgccggct gcacgggccc caagcactct gactgcctgg cctgcctcca cttcaaccac      780
agtggcatct gtgagctgca ctgcccagcc ctggtcacct acaacacaga cacgtttgag      840
tccatgccca atcccgaggg ccggtataca ttcggcgcca gctgtgtgac tgcctgtccc      900
tacaactacc tttctacgga cgtgggatcc tgcacctcg tctgccccct gcacaaccaa      960
gaggtgacag cagaggatgg aacacagcgg tgtgagaagt gcagcaagcc ctgtgcccga     1020
gtgtgctatg gtctgggcat ggagcacttg cgagaggtga gggcagttac cagtgccaat     1080
atccaggagt ttgctggctg caagaagatc tttgggagcc tggcatttct gccggagagc     1140
tttgatgggg acccagcctc caacactgcc ccgctccagc cagagcagct ccaagtgttt     1200
gagactctgg aagagatcac aggttaccta tacatctcag catggccgga cagcctgcct     1260
gacctcagcg tcttccagaa cctgcaagta atccggggac gaattctgca caatggcgcc     1320
tactcgctga ccctgcaagg gctgggcatc agctggctgg ggctgcgctc actgagggaa     1380
ctgggcagtg gactggccct catccaccat aacacccacc tctgcttcgt gcacacggtg     1440
ccctgggacc agctctttcg gaacccgcac caagctctgc tccacactgc caaccggcca     1500
gaggacgagt gtgtgggcga gggctggcc tgccaccagc tgtgcgcccg agggcactgc     1560
tggggtccag ggcccaccca gtgtgtcaac tgcagccagt tccttcgggg ccaggagtgc     1620
gtggaggaat gccgagtact gcaggggctc cccaggggat atgtgaatgc caggcactgt     1680
ttgccgtgcc accctgagtg tcagccccag aatggctcag tgacctgttt tggaccggag     1740
gctgaccagt gtgtggcctg tgcccactat aaggaccctc ccttctgcgt ggcccgctgc     1800
cccagcggtg tgaaacctga cctctcctac atgcccatct ggaagtttcc agatgaggag     1860
ggcgcatgcc agccttgccc catcaactgc acccactcct gtgtggacct ggatgacaag     1920
ggctgccccg ccgagcagag agccagccct ctgacg                                1956
```

<210> SEQ ID NO 3
<211> LENGTH: 117
<212> TYPE: PRT
<213> ORGANISM: Mus musculus

<400> SEQUENCE: 3

```
Gln Val Gln Leu Gln Gln Ser Gly Pro Glu Leu Val Arg Pro Gly Glu
1               5                   10                  15

Ser Val Lys Ile Ser Cys Lys Gly Ser Gly Tyr Thr Phe Thr Asp Tyr
            20                  25                  30

Ala Ile His Trp Val Lys Gln Ser His Ala Lys Ser Leu Glu Trp Ile
        35                  40                  45

Gly Val Phe Ser Ile Tyr Tyr Glu Asn Ile Asn Tyr Asn Gln Lys Phe
    50                  55                  60

Lys Gly Lys Ala Thr Met Thr Val Asp Lys Ser Ser Ser Thr Ala Tyr
65                  70                  75                  80
```

-continued

Leu Asp Leu Ala Arg Leu Thr Ser Glu Asp Ser Ala Ile Tyr Tyr Cys
            85                  90                  95

Ala Arg Arg Asp Gly Gly Thr Ile Asn Tyr Trp Gly Gln Gly Thr Ser
        100                 105                 110

Val Thr Val Ser Ser
        115

<210> SEQ ID NO 4
<211> LENGTH: 351
<212> TYPE: DNA
<213> ORGANISM: Mus musculus

<400> SEQUENCE: 4
caggtccagt tgcagcagtc tggggcctgag ctggtgaggc ctggggaatc agtgaagatt      60
tcctgcaagg gttccggcta cacattcact gattatgcta tacactgggt gaagcagagt     120
catgcaaaga gtctagagtg gattggagtt tttagtattt actatgagaa tataaactac     180
aaccagaagt ttaagggcaa ggccacaatg actgtcgaca atcctccag cacagcctat      240 ttggaccttg ccagattgac atctgaggat tctgccatct attactgtgc aagaagggat     300
ggtgggacta taaactactg gggtcaagga acctcagtca ccgtctcctc a              351

<210> SEQ ID NO 5
<211> LENGTH: 112
<212> TYPE: PRT
<213> ORGANISM: Mus musculus

<400> SEQUENCE: 5

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Trp Thr Phe Gly Gly Gly Thr Lys Leu Glu Ile Lys
            100                 105                 110

<210> SEQ ID NO 6
<211> LENGTH: 336
<212> TYPE: DNA
<213> ORGANISM: Mus musculus

<400> SEQUENCE: 6
gatgttgtga tgacccaaac tccactctcc ctgcctgtca gtcttggaga tcaagcctcc      60
atctcttgca gatctagtca gagccttgta cacagtaatg gaaacactta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatattccg     300
tggacgttcg gtggaggcac caagctggaa atcaaa                               336

<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 990
<212> TYPE: DNA
<213> ORGANISM: Homo sapiens

<400> SEQUENCE: 8
gcgagcacca aggacccttc cgtgtttccc ctcgccccca gctccaaaag caccagcggc         60

```
ggaacagctg ctctcggctg tctcgtcaag gattacttcc ccgagcccgt gaccgtgagc    120
tggaacagcg gagccctgac aagcggcgtc cacaccttcc ctgctgtcct acagtcctcc    180
ggactgtaca gcctgagcag cgtggtgaca gtccctagca gctccctggg cacccagaca    240
tatatttgca acgtgaatca caagcccagc aacaccaagg tcgataagaa ggtggagcct    300
aagtcctgcg acaagaccca cacatgtccc cctgtcccg ctcctgaact gctgggaggc    360
ccttccgtgt tcctgttccc ccctaagccc aaggacaccc tgatgatttc caggacaccc    420
gaggtgacct gtgtggtggt ggacgtcagc cacgaggacc ccgaggtgaa attcaactgg    480
tacgtcgatg gcgtggaggt gcacaacgct aagaccaagc caggggaagga gcagtacaat    540 tccacctaca gggtggtgtc cgtgctgacc gtcctccatc aggactggct gaacggcaaa    600
gagtataagt gcaaggtgag caacaaggcc ctccctgctc ccatcgagaa gaccatcagc    660
aaagccaagg gccagcccag ggaacctcaa gtctataccc tgcctcccag caggggaggag    720 atgaccaaga accaagtgag cctcacatgc ctcgtcaagg gcttctatcc ttccgatatt    780
gccgtcgagt gggagtccaa cggacagccc gagaacaact acaagacaac ccccccgtg    840 ctcgattccg atggcagctt cttcctgtac tccaagctga ccgtggacaa gtccagatgg    900
caacaaggca acgtcttcag ttgcagcgtc atgcatgagg ccctccacaa ccactacacc    960
cagaagagcc tctccctgag ccctggaaag                                    990
```

```
<210> SEQ ID NO 9
<211> LENGTH: 107
<212> TYPE: PRT
<213> ORGANISM: Homo sapiens

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 10
<211> LENGTH: 321
<212> TYPE: DNA
<213> ORGANISM: Homo sapiens

<400> SEQUENCE: 10
agaaccgtcg ccgctcccag cgtcttcatc ttccccccca gcgatgagca gctgaagagc     60
ggaaccgcca gcgtggtgtg cctgctgaac aacttctacc ccagggaggc caaggtgcaa    120
tggaaggtgg acaacgccct acagagcggc aactcccagg agagcgtgac cgagcaggac    180
agcaaggata gcacctacag cctgagcagc accctcaccc tgagcaaggc cgactacgag    240
aagcacaagg tgtacgcctg cgaggtgacc catcagggcc tgagcagccc tgtgaccaag    300
```
agcttcaaca ggggcgagtg c                                                    321

<210> SEQ ID NO 11
<211> LENGTH: 5
<212> TYPE: PRT
<213> ORGANISM: Mus musculus

<400> SEQUENCE: 11

Asp Tyr Ala Ile His
1               5

<210> SEQ ID NO 12
<211> LENGTH: 17
<212> TYPE: PRT
<213> ORGANISM: Mus musculus

<400> SEQUENCE: 12

Val Phe Ser Ile Tyr Tyr Glu Asn Ile Asn Tyr Asn Gln Lys Phe Lys
1               5                   10                  15

Gly

<210> SEQ ID NO 13
<211> LENGTH: 8
<212> TYPE: PRT
<213> ORGANISM: Mus musculus

<400> SEQUENCE: 13

Arg Asp Gly Gly Thr Ile Asn Tyr
1               5

<210> SEQ ID NO 14
<211> LENGTH: 16
<212> TYPE: PRT
<213> ORGANISM: Mus musculus

<400> SEQUENCE: 14

Arg Ser Ser Gln Ser Leu Val His Ser Asn Gly Asn Thr Tyr Leu His
1               5                   10                  15

<210> SEQ ID NO 15
<211> LENGTH: 7
<212> TYPE: PRT
<213> ORGANISM: Mus musculus

<400> SEQUENCE: 15

Lys Val Ser Asn Arg Phe Ser
1               5

<210> SEQ ID NO 16
<211> LENGTH: 9
<212> TYPE: PRT
<213> ORGANISM: Mus musculus

<400> SEQUENCE: 16

Ser Gln Ser Thr His Ile Pro Trp Thr
1               5

<210> SEQ ID NO 17
<211> LENGTH: 117
<212> TYPE: PRT
<213> ORGANISM: Artificial Sequence
<220> FEATURE:
<223> OTHER INFORMATION: heavy  chain variable regions

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Ile His Trp Val Arg Gln Ala Pro Gly Gln Gly Leu Glu Trp Met
        35                  40                  45

Gly Val Phe Ser Ile Tyr Tyr Glu Asn Ile Asn Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Gly Gly Thr Ile Asn Tyr Trp Gly Gln Gly Thr Leu
            100                 105                 110

Val Thr Val Ser Ser
        115

<210> SEQ ID NO 18
<211> LENGTH: 351
<212> TYPE: DNA
<213> ORGANISM: Artificial Sequence
<220> FEATURE:
<223> OTHER INFORMATION: heavy chain variable regions

<400> SEQUENCE: 18
caagtgcagc tggtgcagag cggcgccgag gtgaagaaac ccggtgccag cgtgaaggtg      60
agctgcaagg ccagcggcta caccttcacc gactacgcca tccactgggt gagacaagct     120
cccggtcaag gtctggagtg gatgggcgtg ttcagcatct actacgagaa catcaactac     180
aaccagaagt tcaagggtcg tgtgaccatg accaccgaca ccagcaccag caccgcctac     240
atggagctga gtctttaag aagcgacgac accgccgtgt actactgcgc tcgtagggac      300
ggcggcacca tcaactactg gggccaaggt actttagtga ccgtgagcag c              351

<210> SEQ ID NO 19
<211> LENGTH: 112
<212> TYPE: PRT
<213> ORGANISM: Artificial Sequence
<220> FEATURE:
<223> OTHER INFORMATION: light chain variable regions

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Ile Pro Trp Thr Phe Gly Gln Gly Thr Lys Val Glu Ile Lys
            100                 105                 110

<210> SEQ ID NO 20
<211> LENGTH: 336
<212> TYPE: DNA
<213> ORGANISM: Artificial Sequence
<220> FEATURE:
<223> OTHER INFORMATION: light chain variable regions

<400> SEQUENCE: 20

```
gacgtggtga tgacccagag ccctctgtct ttacccgtga cactgggaca gcccgctagc    60
atcagctgtc gtagcagcca gtctttagtg cactccaacg gcaacaccta tttacactgg   120
ttccagcaga ggcccggcca agcccccaga aggctgatct acaaggtgag caatcgtttc   180
agcggcgtgc ccgacagatt tagcggcagc ggcagcggca ccgactttac tttaaagatc   240
tctcgtgtgg aggccgagga cgtgggcgtg tactactgca gccagagcac ccacatccct   300
tggaccttcg gccaaggtac aaaggtggag atcaag                             336
```

<210> SEQ ID NO 21
<211> LENGTH: 117
<212> TYPE: PRT
<213> ORGANISM: Artificial Sequence
<220> FEATURE:
<223> OTHER INFORMATION: heavy chain variable regions

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Ile His Trp Val Arg Gln Ala Pro Gly Gln Ser Leu Glu Trp Ile
        35                  40                  45

Gly Val Phe Ser Ile Tyr Tyr Glu Asn Ile Asn Tyr Asn Gln Lys Phe
    50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Gly Gly Thr Ile Asn Tyr Trp Gly Gln Gly Thr Leu
            100                 105                 110

Val Thr Val Ser Ser
        115
```

<210> SEQ ID NO 22
<211> LENGTH: 351
<212> TYPE: DNA
<213> ORGANISM: Artificial Sequence
<220> FEATURE:
<223> OTHER INFORMATION: heavy chain variable regions

<400> SEQUENCE: 22

```
caagttcagc tggtgcagag cggagctgag gtgaagaagc ccggcgccag cgtgaaggtg    60
agctgtaagg gcagcggcta ccttcacc gactacgcca tccactgggt gagacaagct    120
cccggtcagt ctttagaatg gatcggcgtg ttcagcatct actacgagaa catcaactat   180
aaccagaagt tcaagggtcg tgccaccatg accgtggaca gagcaccag caccgcctac   240 atggagctga ggtctttaag gagcgacgac accgccgtgt actactgcgc tcgtagggac   300
ggcggcacca tcaactactg gggccaaggt actttagtga cagtgagcag c            351
```

<210> SEQ ID NO 23
<211> LENGTH: 112
<212> TYPE: PRT
<213> ORGANISM: Artificial Sequence
<220> FEATURE:
<223> OTHER INFORMATION: light chain variable regions

<400> SEQUENCE: 23

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Ile Pro Trp Thr Phe Gly Gln Gly Thr Lys Val Glu Ile Lys
            100                 105                 110
```

<210> SEQ ID NO 24
<211> LENGTH: 336
<212> TYPE: DNA
<213> ORGANISM: Artificial Sequence
<220> FEATURE:
<223> OTHER INFORMATION: light chain variable regions

<400> SEQUENCE: 24

```
gacgtggtga tgacccagag cccctttatct ttacccgtta cactgggaca gcccgccagc      60
atcagctgtc gtagcagcca gtctttagtg cacagcaacg gcaacaccta tttacactgg     120
taccagcaga gacccggcca gagccccaga ctgctgatct acaaggtgag caatcgtttc     180
tccggcgtgc ccgacagatt cagcggcagc ggaagcggca ccgacttcac tttaaagatc     240
agcagagtgg aggccgagga cgtgggcgtg tacttctgca gccagagcac ccacatccct     300
tggaccttcg gccaaggtac caaggtggag atcaag                              336
```

<210> SEQ ID NO 25
<211> LENGTH: 120
<212> TYPE: PRT
<213> ORGANISM: Artificial Sequence
<220> FEATURE:
<223> OTHER INFORMATION: heavy chain variable region

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser
        115             120

<210> SEQ ID NO 26
<211> LENGTH: 107
<212> TYPE: PRT
<213> ORGANISM: Artificial Sequence
<220> FEATURE:
<223> OTHER INFORMATION: light chain variable region

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

ANTIBODY BINDING TO HUMAN HER2 AND PREPARATION METHOD AND USE THEREOF

RELATED APPLICATIONS

This application is a national phase application claiming benefit of priority under 35 U.S.C. § 371 to International (PCT) Patent Application serial number PCT/CN2019/098793, filed Aug. 1, 2019, which claims benefit of priority to Chinese Patent Application No. CN 201810861135.5, filed Aug. 1, 2018. The aforementioned applications are expressly incorporated herein by reference in their entirety and for all purposes.

REFERENCE TO ELECTRONIC SEQUENCE LISTING

The application contains a Sequence Listing which has been submitted electronically in .TXT format and is hereby incorporated by reference in its entirety. Said .TXT copy, created on Feb. 8, 2021, is named "SH363-20P450194US_revised sequence listing_ST25.txt" and is 32506 bytes in size. The sequence listing contained in this .TXT file is part of the specification and is hereby incorporated by reference herein in its entirety.

FIELD OF THE INVENTION

The present invention relates to the field of antibodies, and in particular, the present invention discloses an antibody that binds to human HER2, its preparation method and use.

BACKGROUND OF THE INVENTION

HER2/neu (human epidermal growth factor receptor 2), also called erbB2, has tyrosine protein kinase activity and is a member of the human epidermal growth factor receptor family. It is only expressed at low levels in a few normal tissues of adults. However, studies have shown that HER2 is overexpressed in a variety of tumors, for example, such overexpression is present in about 30% of breast cancer patients and 16% of gastric cancer patients. The overexpression of HER2 in tumors can significantly promote tumor angiogenesis, tumor growth, and enhance tumor invasion and metastasis, which is an important indicator of poor prognosis for such patients. Therefore, the first monoclonal antibody drug targeted HER2, Herceptin (Trastuzumab, Genentech/Roche, which has the amino acid sequences of heavy chain variable region and light chain variable region as shown in SEQ ID NOs: 25 and 26, respectively, i.e., SEQ ID NOs: 41 and 42 in U.S. Pat. No. 5,821,337) was approved by the FDA for the treatment of HER2-overexpressing breast cancer and gastric cancer in 1998. Long-term clinical treatment has proved that Herceptin, as the first-line drug for breast cancer treatment, combined with chemotherapy drugs can significantly prolong patient survival and reduce tumor recurrence, but at the later stage of treatment, about 70% of patients still do not respond to Herceptin treatment or develop resistance. In 2012, the FDA approved another monoclonal antibody drug, Perjeta (Pertuzumab, Genentech/Roche) that targets HER2, the action mechanism of which is different from Herceptin. Herceptin mainly blocks the downstream signal transduction of HER2 to cause cell proliferation inhibition, while Perjeta mainly inhibits the formation of HER2 and HER3 heterodimers, so the combination of both has a significantly stronger therapeutic effect on patients than Herceptin alone, but it still does not meet the clinical treatment needs. Therefore, it is still necessary and urgent to continue developing new drugs targeting HER2 to provide more effective treatment regimens for patients with HER2-overexpressing diseases.

SUMMARY OF THE INVENTION

In order to solve the above problems, the inventors of the present invention conducted a large number of experiments, from antigen immunization, hybridoma screening, antibody expression and purification to biological activity identification, and obtained a murine monoclonal antibody 19H6 that specifically binds to human HER2. On the basis above, we further obtained its chimeric antibody 19H6-ch and humanized antibody 19H6-Hu. Unexpectedly, the studies of the present invention show that the binding epitope of 19H6 to human HER2 is different from Herceptin and Perjeta. Experimental results show that the binding epitope of 19H6 is located in the functional domain III (DIII) of the extracellular domain of human HER2 (HER2-ECD). This is the first discovered and reported monoclonal antibody for treatment that can specifically bind to the functional DIII of human HER2-ECD. Before the studies of this present invention, the structure and properties of the monoclonal antibody that can bind to the functional DIII of human HER2-ECD were still unclear. The present invention further confirmed the key site affecting the binding of 19H6 to human HER2-ECD. The experimental results at the cellular level show that the combination of 19H6 and Herceptin can significantly inhibit proliferation of breast cancer cells BT474, SKBR3 and gastric cancer cells NCI-N87 in vitro, and has significantly better effect than the combination of Perjeta and Herceptin. Furthermore, the experimental results of the chimeric antibody 19H6-ch and the humanized antibody 19H6-Hu show that they have anti-tumor biological activities comparable to that of 19H6 at the cellular level. In vivo experimental results show that the combination of 19H6-Hu and Herceptin has significantly better anti-tumor activity than Herceptin alone in the xenograft tumor models of Herceptin sensitive cell NCI-N87 and resistant cell HCC1954. And the combination of 19H6-Hu and Herceptin also has significantly better efficacy than the combination of Perjeta and Herceptin in HCC1954 xenograft tumor model. Therefore, the antibody that binds to human HER2 with a novel HER2 binding epitope developed by the present invention is expected to become a better potential therapeutic drug for patients with HER2-overexpressing diseases.

Therefore, a first object of the present invention is to provide an antibody or antigen-binding fragment thereof that binds to human HER2.

A second object of the present invention is to provide another antibody or antigen-binding fragment thereof that binds to human HER2.

A third object of the present invention is to provide another antibody or antigen-binding fragment thereof that binds to human HER2.

A fourth object of the present invention is to provide a nucleotide sequence encoding the antibody or antigen-binding fragment thereof that binds to human HER2.

A fifth object of the present invention is to provide an expression vector comprising the nucleotide sequence.

A sixth object of the present invention is to provide a host cell comprising the expression vector.

A seventh object of the present invention is to provide a method of preparing the antibody or antigen-binding fragment thereof that binds to human HER2.

An eighth object of the present invention is to provide a pharmaceutical composition comprising the antibody or antigen-binding fragment thereof that binds to human HER2.

A ninth object of the present invention is to provide the use of the antibody or antigen-binding fragment thereof that binds to human HER2 or the pharmaceutical composition.

In order to achieve the above objects, the present invention adopts the following technical solutions:

The first aspect of the present invention provides an antibody or antigen-binding fragment thereof that binds to human HER2, the human HER2 epitope which it binds to is located in the third functional domain III of the extracellular domain of human HER2 and comprises one or more of the following amino acid residues: D502, V505, E507 or L509 of SEQ ID NO: 1.

According to a preferred embodiment of the present invention, the human HER2 epitope comprises an amino acid residue selected from the group consisting of:
(a) D502 of SEQ ID NO: 1;
(b) V505 of SEQ ID NO: 1;
(c) E507 of SEQ ID NO: 1;
(d) L509 of SEQ ID NO: 1;
(e) D502 and V505 of SEQ ID NO: 1;
(f) D502 and E507 of SEQ ID NO: 1;
(g) D502 and L509 of SEQ ID NO: 1;
(h) V505 and E507 of SEQ ID NO: 1;
(i) V505 and L509 of SEQ ID NO: 1;
(j) E507 and L509 of SEQ ID NO: 1;
(k) D502, V505 and E507 of SEQ ID NO: 1;
(l) D502, V505 and L509 of SEQ ID NO: 1;
(m) V505, E507 and L509 of SEQ ID NO: 1; and
(n) D502, V505, E507 and L509 of SEQ ID NO: 1.

The second aspect of the present invention provides an antibody or antigen-binding fragment thereof that binds to human HER2, and the human HER2 epitope which it binds to is located in the third functional domain III of the extracellular domain of human HER2 and has the amino acid sequence as shown in positions 499-510 of SEQ ID NO: 1.

According to the present invention, the third functional domain III of the extracellular domain of human HER2 has the amino acid sequence as shown in positions 343-510 of SEQ ID NO: 1.

The third aspect of the present invention provides an antibody or antigen-binding fragment thereof that binds to human HER2, comprising:
(a) heavy chain complementarity determining regions HCDR1, HCDR2, HCDR3, the HCDR1 having the amino acid sequence as shown in SEQ ID NO: 11, the HCDR2 having the amino acid sequence as shown in SEQ ID NO: 12, and the HCDR3 having the amino acid sequence as shown in SEQ ID NO: 13, and
(b) light chain complementarity determining regions LCDR1, LCDR2, LCDR3, the LCDR1 having the amino acid sequence as shown in SEQ ID NO: 14, the LCDR2 having the amino acid sequence as shown in SEQ ID NO: 15, and the LCDR3 having the amino acid sequence as shown in SEQ ID NO: 16.

According to the present invention, the antibody is a monoclonal antibody or a polyclonal antibody. Preferably, the antibody is a monoclonal antibody.

According to the present invention, the antibody is a murine antibody, a chimeric antibody or a humanized antibody.

According to the present invention, the antigen-binding fragment includes a Fab fragment, a F(ab)'2 fragment, a Fv fragment, a single chain antibody (scFv) and a single domain antibody (sdAb), etc.

According to the present invention, the antibody or antigen-binding fragment thereof that binds to human HER2 can inhibit the proliferation of tumor cells overexpressing HER2. Preferably, the tumor cells include breast cancer cell BT474, breast cancer cell SKBR3, gastric cancer cell NCI-N87, and breast cancer cell HCC1954.

According to a preferred embodiment of the present invention, the antibody or antigen-binding fragment thereof that binds to human HER2 comprises a heavy chain variable region having the amino acid sequence as shown in SEQ ID NO: 3, and a light chain variable region having the amino acid sequence as shown in SEQ ID NO: 5; or the antibody or antigen-binding fragment thereof that binds to human HER2 comprises a heavy chain variable region having the amino acid sequence as shown in SEQ ID NO: 17, and a light chain variable region having the amino acid sequence as shown in SEQ ID NO: 19; or the antibody or antigen-binding fragment thereof that binds to human HER2 comprises a heavy chain variable region having the amino acid sequence as shown in SEQ ID NO: 21, and a light chain variable region having the amino acid sequence as shown in SEQ ID NO: 23.

According to a preferred embodiment of the present invention, the antibody or antigen-binding fragment thereof that binds to human HER2 comprises a heavy chain constant region having the amino acid sequence as shown in SEQ ID NO: 7, and a light chain constant region having the amino acid sequence as shown in SEQ ID NO: 9.

The fourth aspect of the present invention provides an isolated nucleic acid, which encodes the antibody or antigen-binding fragment thereof that binds to human HER2 as described in any one of the above.

According to a preferred embodiment of the present invention, the nucleic acid has the nucleotide sequence encoding the heavy chain variable region as shown in SEQ ID NO: 4, and the nucleotide sequence encoding the light chain variable region as shown in SEQ ID NO: 6; or the nucleotide has the nucleotide sequence encoding the heavy chain variable region as shown in SEQ ID NO: 18, and the nucleotide sequence encoding the light chain variable region as shown in SEQ ID NO: 20; or the nucleic acid has the nucleotide sequence encoding the heavy chain variable region as shown in SEQ ID NO: 22, and the nucleotide sequence encoding the light chain variable region as shown in SEQ ID NO: 24.

According to a preferred embodiment of the present invention, the nucleic acid has the nucleotide sequence encoding the heavy chain constant region as shown in SEQ ID NO: 8, and the nucleotide sequence encoding the light chain constant region as shown in SEQ ID NO: 10.

The fifth aspect of the present invention provides an expression vector, which comprises the nucleotide sequence as described in any one of the above.

The sixth aspect of the present invention provides a host cell, which comprises the expression vector as described above.

The seventh aspect of the present invention provides a method of preparing the antibody or antigen-binding fragment thereof that binds to human HER2 as described above, which comprises the following steps:

a) under the condition of expression, the host cells as described above are cultured to express the antibody or antigen binding fragment of the antibody binding to human HER2;

b) isolating and purifying the antibody or antigen-binding fragment thereof that binds to human HER2 of step a).

The eighth aspect of the present invention provides a pharmaceutical composition, which comprises the antibody or antigen-binding fragment thereof that binds to human HER2 as described in any one of the above, and a pharmaceutically acceptable carrier.

According to a preferred embodiment of the present invention, the pharmaceutical composition further comprises a second antibody or antigen-binding fragment thereof that binds to human HER2.

According to a preferred embodiment of the present invention, the second antibody or antigen-binding fragment thereof that binds to human HER2 does not bind to the third functional domain III of the extracellular domain of human HER2, and the third functional domainIII has the amino acid sequence as shown in positions 343-510 of SEQ ID NO: 1.

According to a preferred embodiment of the present invention, the second antibody or antigen-binding fragment thereof that binds to human HER2 binds to the fourth functional domain IV of the extracellular domain of human HER2, and the fourth functional domain IV has the amino acid sequence as shown in positions 511-582 of SEQ ID NO:1.

According to a preferred embodiment of the present invention, the second antibody or antigen-binding fragment thereof that binds to human HER2 comprises a heavy chain variable region and a light chain variable region, and the heavy chain variable region has the amino acid sequence as shown in SEQ ID NO: 25, the light chain variable region has the amino acid sequence as shown in SEQ ID NO: 26.

According to a preferred embodiment of the present invention, the second antibody or antigen-binding fragment thereof that binds to human HER2 is trastuzumab.

The ninth aspect of the present invention provides the use of the antibody or antigen-binding fragment thereof that binds to human HER2 as described in any one of the above or the pharmaceutical composition as described in any one of the above in the preparation of a pharmaceutical composition for the treatment of HER2-overexpressing diseases.

According to a preferred embodiment of the present invention, the HER2-overexpressing disease is cancer. More preferably, the cancer includes breast cancer, gastric cancer, ovarian cancer, and so on.

Beneficial effects:

The selected antibody or antigen-binding fragment thereof that binds to human HER2 obtained by the present invention can specifically bind to human HER2. Compared with the known Perjeta, its combination with Herceptin has better biological activity of inhibiting the proliferation of HER2-overexpressing tumor cells. It has an antigen-binding epitope that is different from known antibodies that bind to human HER2. It can be used to prepare medicaments for treating HER2-overexpressing diseases, such as cancer and have good prospect of clinical application.

DESCRIPTION OF THE FIGURES

FIG. 1 shows the proliferation inhibition results of 14 candidate murine anti-human HER2 monoclonal antibodies combined with Herceptin on breast cancer cells BT474, wherein.

FIG. 2 shows the proliferation inhibition results of 14 candidate murine anti-human HER2 monoclonal antibodies combined with Herceptin on breast cancer cells SKBR3, wherein.

FIG. 8 shows the epitope competition results of murine monoclonal antibody 19H6, Herceptin and Perjeta on human HER2-ECD determined by competitive ELISA, wherein.

FIG. 10 shows the binding results of murine monoclonal antibody 19H6 to various functional domains of human HER2-ECD determined by Western blot and ELISA, wherein.

FIG. 21 shows the SDS-PAGE electrophoresis results of humanized antibodies 19H6-Hu and 19H6-graft, wherein.

FIG. 29-FIG. 31 show the effect of 19H6-Hu on HER2-related signaling pathways determined by Western blot, wherein, FIG. 29 shows the effect on breast cancer cells BT474;
FIG. 30 shows the effect on SKBR3 cells;
FIG. 31 shows the effect on gastric cancer cells NCI-N87.

DETAILED DESCRIPTION OF THE INVENTION

Figure 1A:
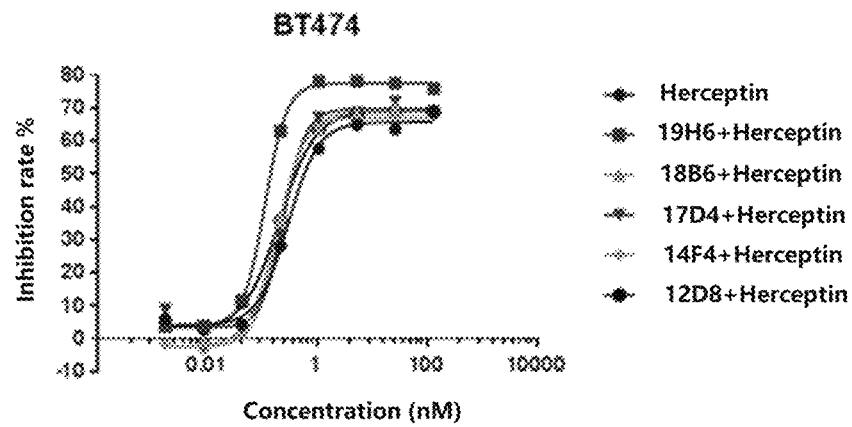
FIG. 1A: the treatment group of 19H6, 18B6, 17D4, 14F4 and 12D8 combined with Herceptin.

In the present invention, the terms "antibody (Ab)" and "immunoglobulin G (IgG)" are heterotetrameric glycoproteins of about 150,000 daltons with identical structural characteristics, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable region (VH) followed by constant regions. Each light chain has a variable region (VL) at one end and a constant region at its other end; the constant region of the light chain is aligned with the first constant region of the heavy chain, and the light chain variable region is aligned with the variable region of the heavy chain. The antibodies of the present invention include monoclonal antibodies, polyclonal antibodies, multispecific antibodies (such as bispecific antibodies) formed by at least two antibodies, antigen-binding fragments of antibodies, etc. The antibodies of the present invention comprise murine antibodies, chimeric antibodies, humanized antibodies, etc.

In the present invention, the term "monoclonal antibody (mAb)" refers to an antibody obtained from a population of substantially homogeneous antibodies, that is, the individual antibodies contained in the population are the same, except for a few possible naturally occurring mutations. Monoclonal antibodies target a single antigen site with high specificity. Moreover, unlike conventional polyclonal antibody preparations (usually with different antibodies directed against different antigenic determinants), each monoclonal antibody is directed against a single determinant on the antigen. In addition to their specificity, the benefit of monoclonal antibodies is that they are synthesized by the culture of hybridoma cells and are not contaminated by other immunoglobulins. The modifier "monoclonal" indicates the characteristics of an antibody, which is obtained from a substantially uniform antibody population, and it should not be interpreted as requiring any special method to produce antibodies.

In the present invention, the term "murine antibody" refers to an antibody derived from rat or mouse, preferably mouse. The murine antibody of the present invention is obtained by immunizing mice with the extracellular domain of human HER2 as an antigen and screening hybridoma cells. More preferably, the murine antibody of the present invention includes 1H10, 2C5, 4A4, 10C4, 11D10, 12D8, 14F4, 17D4, 18B6, 19H6, 25H10, 27D1, 30A1 and 33B5. Most preferably, the murine antibody of the present invention is 19H6.

In the present invention, the term "chimeric antibody" refers to an antibody that comprises heavy and light chain variable region sequences from one species and constant region sequences from another species, such as an antibody having mouse heavy and light chain variable regions linked to human constant region. Preferably, the chimeric antibody of the present invention is obtained by splicing the heavy chain variable region sequence and the light chain variable region sequence of the murine antibody 19H6 with the human constant region. More preferably, the heavy chain of the chimeric antibody of the present invention is obtained by splicing the heavy chain variable region sequence of the murine antibody 19H6 with the constant region of human IgG1, and the light chain is obtained by splicing the light chain variable region sequence of the murine antibody 19H6 with human kappa chain. Most preferably, the chimeric antibody of the present invention is 19H6-ch.

In the present invention, the term "humanized antibody" means that the CDR is derived from a non-human (preferably, mouse) antibody, while the remaining parts (including framework regions and constant regions) are derived from human antibody. In addition, framework region residues may be altered to preserve the binding affinity. Preferably, the humanized antibody of the present invention is obtained by recombining the CDR region of the murine antibody 19H6 and the non-CDR region derived from a human antibody, and subjecting the embedded residues, the residues that directly interact with the CDR region, and the residues that have important influence on the conformation of VL and VH of 19H6 to back mutation. More preferably, the humanized antibody of the present invention includes 19H6-Hu and 19Hu-graft. Most preferably, the humanized antibody of the present invention is 19H6-Hu.

In the present invention, the term "antigen-binding fragment" refers to a fragment of an antibody capable of specifically binding to an epitope of human HER2. Examples of the antigen-binding fragments of the present invention include Fab fragments, F(ab')2 fragments, Fv fragments, single chain antibodies (scFv), single domain antibodies (sdAb), etc. A Fab fragment is a fragment produced by digesting an antibody with papain. An F(ab')2 fragment is a fragment produced by digesting an antibody with pepsin. An Fv fragment is composed of dimers in which the variable region of the heavy chain and the variable region of the light chain of an antibody are closely and non-covalently linked. A single-chain antibody (scFv) is an antibody in which the variable region of the heavy chain and the variable region of the light chain of an antibody are linked by a short peptide (linker) of 15-20 amino acids. A single domain antibody (sdAb), also called nanobody or heavy chain antibody, is composed of heavy chain only, and its antigen binding region is only a single domain linked to the Fc region through a hinge region.

In the present invention, the term "variable" refers to the fact that certain portions of the antibodies' variable regions differ in sequences, which is responsible for the binding specificity of various specific antibodies to their specific antigens. However, the variability is not evenly distributed in the variable regions of antibodies. It is concentrated in three segments called complementarity determining regions (CDRs) or hypervariable regions both in light chain and heavy chain variable regions. The relatively conserved portions of the variable regions are called the framework regions (FR). The variable regions of native heavy and light chains comprise respectively four FR regions, mostly in β-sheet configuration, and connected by three CDRs, in some cases forming partial β-sheet structure. The CDRs in each chain are held together closely through the FR regions and, forming the antigen binding site of antibodies with CDRs from another chain (see Kabat et al., NIH Publ.No.91-3242, Volume I, Pages 647-669 (1991)). The constant regions are not involved directly in binding an antibody to an antigen, but they exhibit various effector functions, such as participation of antibody-dependent cell-mediated cytotoxicity (ADCC) and the like.

In the present invention, the terms "epitope" and "human HER2 epitope" refer to the region located on human HER2 and specifically binding to an antibody. Preferably, the human HER2 epitope of the present invention is located in the extracellular domain of human HER2. The extracellular domain of human HER2 has the amino acid sequence as shown in SEQ ID NO: 1. Preferably, the human HER2 epitope of the present invention is located in the third functional domain III of the extracellular domain of human HER2, and the third functional domain III has the amino acid sequence as shown in positions 343-510 of SEQ ID NO: 1. More preferably, the human HER2 epitope of the present invention includes one or more of the following residues: D502, V505, E507 or L509 of SEQ ID NO: 1. More preferably, the human HER2 epitope of the present invention has the amino acid sequence as shown in positions 499-510 of SEQ ID NO: 1.

In the present invention, the terms "antibody or antigen-binding fragment thereof that binds to human HER2" and "anti-human HER2 antibody or antigen-binding fragment thereof" refer to an antibody or antigen-binding fragment thereof that can specifically bind to human HER2 epitopes, while cannot cross-react with other human epidermal growth factor receptor family members (HER1, HER3, HER4). Preferably, the antibody or antigen-binding fragment thereof that binds to human HER2 of the present invention is capable of inhibiting the proliferation of HER2-overexpressing tumor cells (such as breast cancer cells BT474, SKBR3 and HCC1954, and gastric cancer cells NCI-N87, etc.).

In the present invention, the term "expression vector" may be pTT5, pSECtag series, pCGS3 series, pCDNA series vectors, etc., as well as other vectors used in mammalian expression systems, etc. The expression vector comprises a fusion DNA sequence connected with appropriate transcription and translation regulatory sequences.

In the present invention, the term "host cell" refers to a cell suitable for expressing the expression vector as described above. It may be a eukaryotic cell, for example, mammalian or insect host cell culture system may be used to express the fusion protein of the present invention, CHO (Chinese hamster Ovary), HEK293, COS, BHK, etc. as well as derived cells of the above-mentioned cells are all applicable to the present invention.

In the present invention, the terms "cell" and "cell line" may be used interchangeably.

In the present invention, the term "pharmaceutical composition" means that the antibody or antigen-binding fragment thereof that binds to human HER2 of the present invention can be combined with a pharmaceutically acceptable carrier to form a pharmaceutical preparation composition, so as to exert a therapeutic effect more stably. These preparations can ensure the conformational integrity of the amino acid core sequences of the antibody or antigen-binding fragment thereof that binds to human HER2 disclosed in the present invention, and meanwhile, protect the multifunctional groups of the protein from degradation (including but not limited to aggregation, deamination or oxidation). Preferably, the pharmaceutical composition of the present invention further comprises a second antibody or antigen-binding fragment thereof that binds to human HER2. More preferably, the second antibody or antigen-binding fragment thereof that binds to human HER2 does not bind to the third functional domain III of the extracellular domain of human HER2, and the third functional domain III has the amino acid sequence as shown in positions 343-510 of SEQ ID NO: 1. More preferably, the second antibody or antigen-binding fragment thereof that binds to human HER2 binds to the fourth functional domain IV of the extracellular domain of human HER2, and the fourth functional domain IV has the amino acid sequence as shown in positions 511-582 of SEQ ID NO: 1. More preferably, the second antibody or antigen-binding fragment thereof that binds to human HER2 comprises a heavy chain variable region and a light chain variable region, and the heavy chain variable region has the amino acid sequence as shown in SEQ ID NO: 25, the light chain variable region has the amino acid sequence as shown in SEQ ID NO: 26. More preferably, the second antibody or antigen-binding fragment thereof that binds to human HER2 is trastuzumab.

In the present invention, the term "HER2-overexpressing disease" means that the expression level of HER2 in cells in an abnormal disease state is higher than the expression level of HER2 in normal cells of the same tissue type. The HER2-overexpressing disease of the present invention comprises HER2-overexpressing cancers, including but not limited to breast cancer, gastric cancer, ovarian cancer, etc.

The following examples and experimental examples further illustrate the present invention and should not be construed as limiting the present invention. The examples do not include a detailed description of traditional methods, such as those methods of constructing expression vectors and preparing plasmids, methods of inserting genes encoding proteins into such vectors and plasmids, or methods of transfecting plasmids into host cells. Such methods are well known to those of ordinary skill in the art, and are described in many publications, including Sambrook, J., Fritsch, E. F. and Maniais, T. (1989) Molecular Cloning: A Laboratory Manual, 2nd edition, Cold spring Harbor Laboratory Press.

The cell lines with high HER2 expression used in the following examples included breast cancer cells BT474, breast cancer cells SKBR3, gastric cancer cells NCI-N87, and breast cancer cells HCC1954, wherein HCC1954 (Catalog No.: ATCC® CRL-2338™) and SKBR3 (Catalog No.: ATCC® HTB-30™) were purchased from the American Type Culture Collection (ATCC), BT474 (Catalog No.: TCHu143) and NCI-N87 (Catalog No.: SCSP-534) were purchased from the Cell Bank of the Chinese Academy of Sciences, and they were cultured according to the corresponding instructions.

The positive control antibodies used in the following examples was Herceptin (purchased from Roche, 440 mg/20 ml, Lot No. N3723) and Perjeta (purchased from Roche, 420 mg/14 ml, Lot No. H0248B02).

The human HER2-ECD protein used in the following examples was prepared according to the following method: The nucleic acid sequence of human HER2-ECD (1 to 652 amino acids of NCBI Accession No. NP_004439.2, the amino acid sequence as shown in SEQ ID NO: 1, the nucleotide sequence as shown in SEQ ID NO: 2) added with a 6×His tag at the C-terminus was cloned into the pTT5 vector (purchased from NRC biotechnology Research Institute) to construct HER2-ECD-His-pTT5, and transfected into Chinese hamster ovary (CHO) cells for expression. 7 days after transfection, the expressed supernatant was collected and purified for use.

In the following embodiments, the abbreviated terms are defined and explained as follows:
HAT: hypoxantin, aminopterin and thymidin;
PBS: 10 mM phosphate buffer saline;
PBST: 10 mM phosphate buffer saline containing 0.05% Tween 20;
TBS: Tris-HCl buffered salt solution, pH=7.5;
TBST: TBS solution containing 0.1% Tween 20;
BSA: Bovine serum albumin;
TMB: 3,3',5,5'-Tetramethylbenzidine;
HRP: Horseradish Peroxidase;
DTT: DL-Dithiothreitol.

Example 1 Preparation of Murine Monoclonal Antibody that Specifically Binds to Human HER2

1.1 Mouse Immunization

Balb/c mice (purchased from Shanghai Lingchang Biotechnology Co., Ltd.) were routinely immunized with human HER2-ECD protein (homemade, purity>95%) that was expressed by mammalian cells-Chinese hamster ovary (CHO) cells. On day 1, soluble human HER2-ECD protein was emulsified with Freund's complete adjuvant, and then administered to Balb/c mice by multi-point subcutaneous injection (human HER2-ECD 50 μg/mouse/0.5 mL). On day 21, soluble human HER2-ECD protein was emulsified with Freund's incomplete adjuvant, and then administered to Balb/c mice by subcutaneous injection (human HER2-ECD 50 μg/mouse/0.5 mL). On day 41, soluble human HER2-ECD protein, 50 μg/mouse/0.2 mL, was injected intraperitoneally. 3-4 days later, the mouse spleens were taken for fusion experiment.

1.2 Preparation and Screening of Hybridoma Cells 3-4 days after the last immunization of the mice, the mouse spleen cells and the mouse myeloma cells SP2/0 were electrofused with an electrofusion device (purchased from BTX) using conventional hybridoma technology. The fused cells were mixed evenly in complete medium (that was, RPMI1640 and DMEM F12 medium were mixed at a ratio of 1:1, added with 1% glutamine, 1% sodium pyruvate, 1% MEM-NEAA (minimal basic medium-non-essential amino acid solution), 1% penicillin-streptomycin, 50 μM β-mercaptoethanol and 20% FBS (fetal bovine serum); all products were purchased from Gibco), divided into a total of 36 96-well culture plates at $10^5$ cells/100 μL/well and cultured overnight. On the next day, each well was added with 100 μL of complete medium containing 2×HAT, to allow the culture medium in the 96-well plates to be 200 μL/well (containing 1×HAT). 7-12 days later, the supernatant was harvested, and the hybridoma wells with binding activity to human HER2-ECD were screened by indirect enzyme-linked immunosorbent assay (ELISA), and a total of 839 positive wells were obtained. By the method of detecting the inhibition of the hybridoma wells on the proliferation of breast cancer cell line BT474, 36 positive wells were further screened. The hybridoma having binding activity to human HER2-ECD and inhibition on BT474 cell proliferation were subjected to the first and second rounds of subcloning by the limiting dilution method. Finally, we obtained 14 positive clone hybridoma cell strains, named 1H10, 2C5, 4A4, 10C4, 11D10, 12D8, 14F4, 17D4, 18B6, 19H6, 25H10, 27D1, 30A1 and 33B5.

Wherein, the method of screening the hybridoma supernatant with binding activity to human HER2-ECD by indirect enzyme-linked immunosorbent assay was as follows: the recombinant human HER2-ECD protein was diluted to 1 μg/mL with a coating solution (50 mM carbonate coating buffer, pH 9.6), and added to the ELISA plate at 100 μL/well for coating overnight at 4° C. The plate was washed with PBST 3 times, added with a blocking solution (2% BSA-PBS) at 200 μL/well, placed at 37° C. for 1 h then washed once with PBST for use. The collected hybridoma supernatant was sequentially added to the blocked ELISA plate, 100 L/well, and incubated at 37° C. for 1 h. The plate was washed three times with PBST, added with HRP-labeled goat anti-mouse IgG secondary antibody (purchased from Millipore, product number AP181P), and incubated at 37° C. for 30 min. The plate was washed five times with PBST, and pat dry on absorbent paper to remove the remaining droplets. 100 μL of TMB (purchased from BD, Product No. 555214) was added to each well, and placed at room temperature (20±5° C.) in the dark for 5 min. 50 μL of 2M $H_2SO_4$ stop solution was added to each well to stop the substrate reaction. The OD value was read at 450 nm with a microplate reader, and the binding activity of the antibody to be tested with the target antigen HER2-ECD was analyzed.

Wherein, the method of detecting the proliferation inhibition of hybridoma supernatant on breast cancer cell line BT474 was as follows: The breast cancer cells BT474 in the logarithmic growth phase were digested with trypsin, counted, resuspended in complete medium containing 10% fetal bovine serum and plating on a 96-well cell culture plate with 5000 BT474 cells per well, 150 μL/well, incubated in a cell incubator at 37° C., 5% $CO_2$ for 16 h. Different concentrations of the antibody to be tested were added, and 3 replicate wells for each drug concentration were provided.

After treatment for 6 days, the culture solution was discarded, CCK-8 (Cell counting kit-8, purchased from Dojindo, Cat #CK04) reaction solution was added, 100 μL/well, reacted at 37° C. until the expected color shade appeared. The cell viability of each group was measured (OD450 nm). The culture well without cells was set as the blank well, and the culture well with cells but without drug was set as the control well. The relative cell survival rate and growth inhibition rate were calculated according to the following formulas and analysis was performed by Graph-Pad Prism 6 software:

Relative survival rate=(OD administration−OD blank)/(OD control−OD blank)×100%.

Growth inhibition rate=1−relative survival rate.

1.3 Preparation and Identification of Murine Anti-Human HER2 Monoclonal Antibody The 14 hybridoma cell strains screened in Example 1.2 were amplified in a serum-containing complete medium, centrifuged to change the medium to a serum-free medium (SFM, purchased from Life Technologies, Cat. No. 12045-076), allowing the cell density to be $1{\sim}2{\times}10^7$/mL, cultured for 1 week under the condition of 5% $CO_2$, 37° C., centrifuged to obtain the culture supernatant, purified by Protein G affinity chromatography, to obtain 14 strains of murine anti-human HER2 monoclonal antibodies.

By the method of combining with Herceptin to inhibit the proliferation of breast cancer cells BT474 and SKBR3, 14 candidate murine anti-human HER2 monoclonal antibodies were further screened. A 96-well cell culture plate was seeded according to 5000 BT474 cells or 3000 SKBR3 cells per well, 150 μL/well, and cultured in a 37° C., 5% $CO_2$ cell incubator for 16 h. The antibodies to be tested and Herceptin diluted in a 3-fold gradient with cell complete medium were added. The highest working concentration of each antibody was 20 μg/mL. The combined administration group of Herceptin and the single administration group of Herceptin were set up. Data processing and analysis methods refer to the one described in Example 1.2.

Figure 1B:
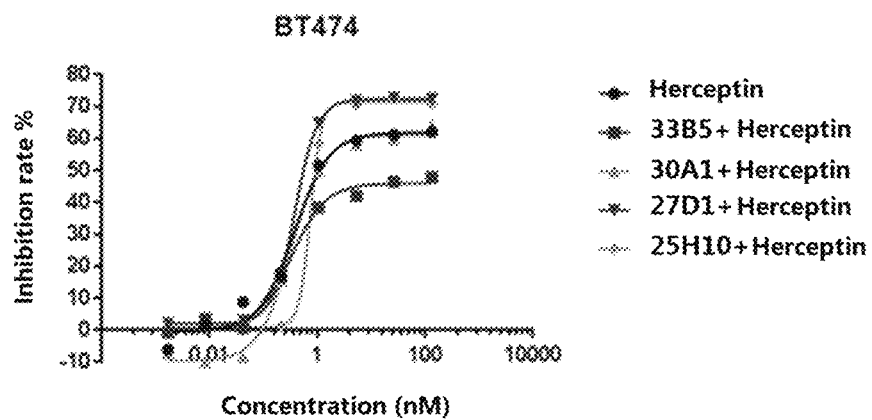
FIG. 1B: the treatment group of 33B5, 30A1, 27D1 and 25H10 combined with Herceptin.
Figure 1C:
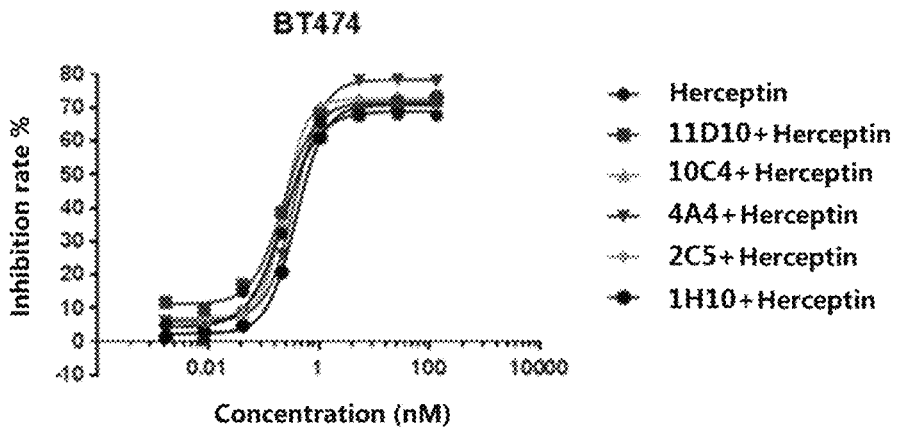
FIG. 1C: the treatment group of 11D10, 10C4, 4A4, 2C5 and 1H10 combined with Herceptin.

The results are shown in FIGS. 1A-1C. 4 monoclonal antibodies, namely 27D1, 25H10, 4A4 and 19H6, can significantly cooperation with Herceptin to inhibit the proliferation of BT474 cells, so that the maximum inhibition rate of Herceptin on BT474 was significantly increased, and the drug concentration that achieves the maximum inhibition rate of single Herceptin was greatly reduced, especially 19H6.

Figure 2A:
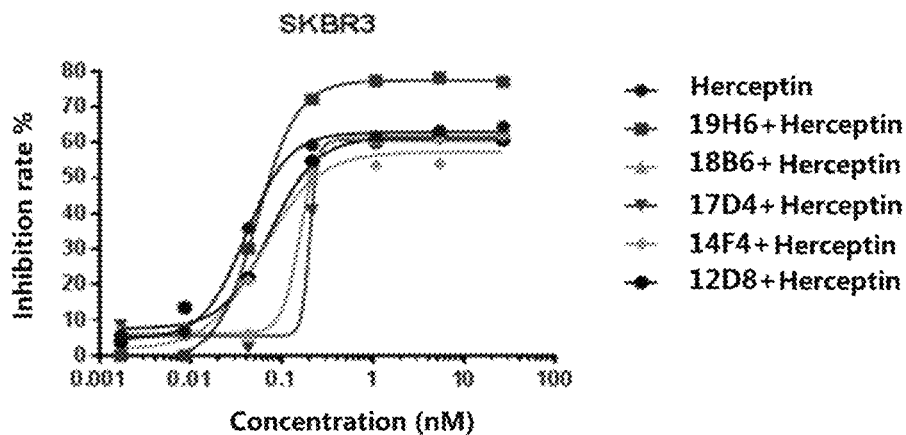
FIG. 2A shows the treatment group of 19H6, 18B6, 17D4, 14F4 and 12D8 combined with Herceptin.
Figure 2B:
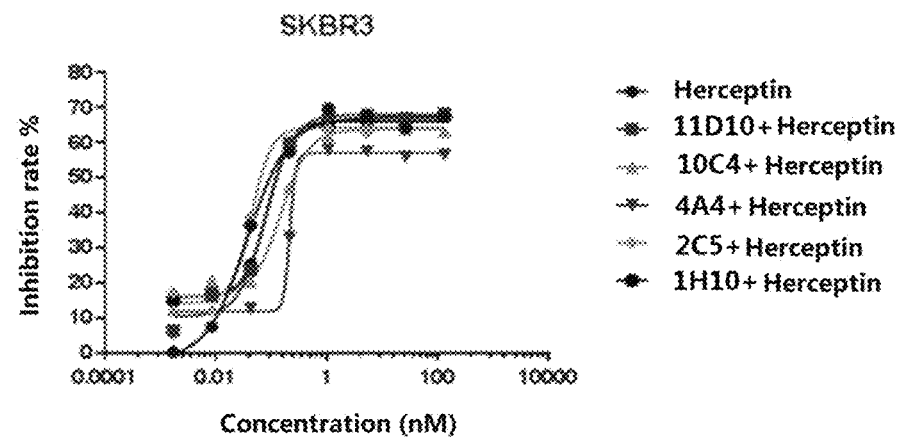
FIG. 2B shows the treatment group of 11D10, 10C4, 4A4, 2C5 and 1H10 combined with Herceptin.
Figure 2C:
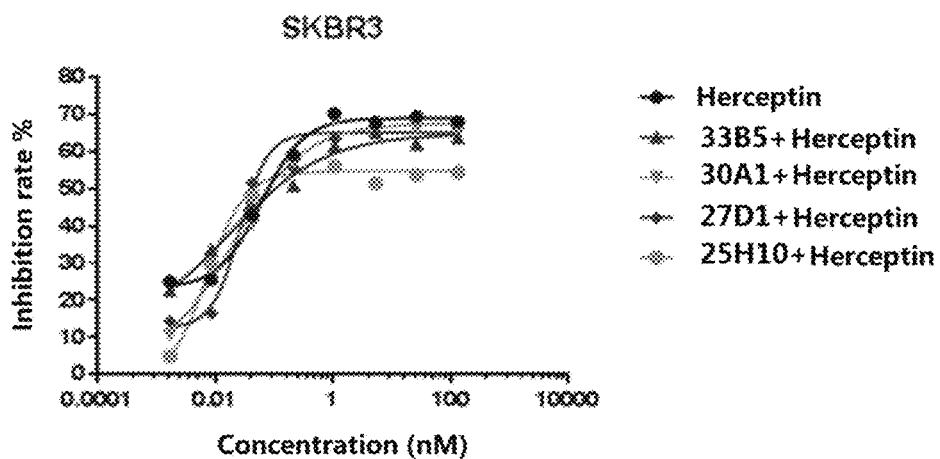
FIG. 2C shows the treatment group of 33B5, 30A1, 27D1 and 25H10 combined with Herceptin.

The results are shown in FIGS. 2A-2C. One of the monoclonal antibodies, namely 19H6, can significantly cooperation with Herceptin to inhibit the proliferation of SKBR3 cells, so that the maximum growth inhibition rate on SKBR3 cells was significantly increased. The other 3 monoclonal antibodies, namely 4A4, 25H10, 27D1, although can cooperate with Herceptin to inhibit the proliferation of BT474 cells, they cannot significantly cooperation with Herceptin to inhibit the proliferation of SKBR3 cells.

Based on the above screening results, the murine anti-human HER2 monoclonal antibody 19H6 was selected for mass preparation according to the above method for subsequent in vivo biological activity and other experiments.

Example 2 In Vitro Activity Determination of Murine Anti-Human HER2 Monoclonal Antibody 19H6

2.1 Determination of Binding Affinity of Murine Antibody 19H6 to Target Antigen

In this example, the binding affinity of 19H6 to human HER2-ECD was determined by ELISA.

The experimental method refers to Example 1.2.

Figure 3:
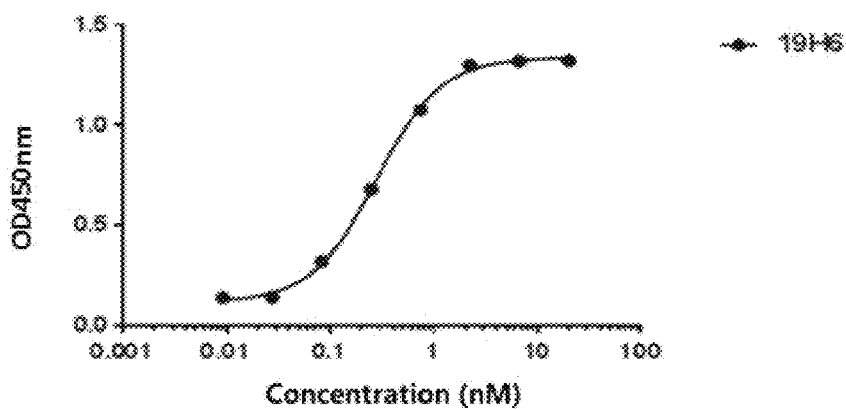
FIG. 3 shows the binding affinity of murine monoclonal antibody 19H6 to human HER2-ECD determined by ELISA.

The results are shown in FIG. 3. The results show that 19H6 can specifically bind to human HER2. In this detection system, the EC50 for binding was 0.28 nM.

2.2 Determination of Binding Affinity of Murine Antibody 19H6 to Target Cells

In this example, the binding affinity of 19H6 to breast cancer cells BT474 was determined by Fluorescence activated Cell Sorting (FACS).

In this experiment, breast cancer cells BT474 were used as target cells. 100 μL of 19H6, which was serially diluted 12 gradients from 1000 nM in a 3-fold gradient was used as the primary antibody, and incubated with $3\times10^5$ BT474 cells, which was suspended in 100 μL RPMI-1640 serum-free medium (purchased from Gibco, Cat. No. 22400089) at 4° C. for 1 h, respectively. (The maximum working concentration of 19H6 was 500 nM). The cells were washed twice with PBS to remove unbound 19H6, and then the cells were incubated with 200 μL, 2 μg/mL, FITC-labeled anti-mouse Fc secondary antibody (purchased from BD Biosciences, Cat. No. 554001) at 4° C. for 30 min. The cells were washed twice with PBS to remove unbound secondary antibody, and finally the cells were resuspended in 200 μL PBS. The binding affinity of 19H6 to the cells was measured by flow cytometry, and the data obtained was analyzed by GraphPad Prism 6 software.

Figure 4:
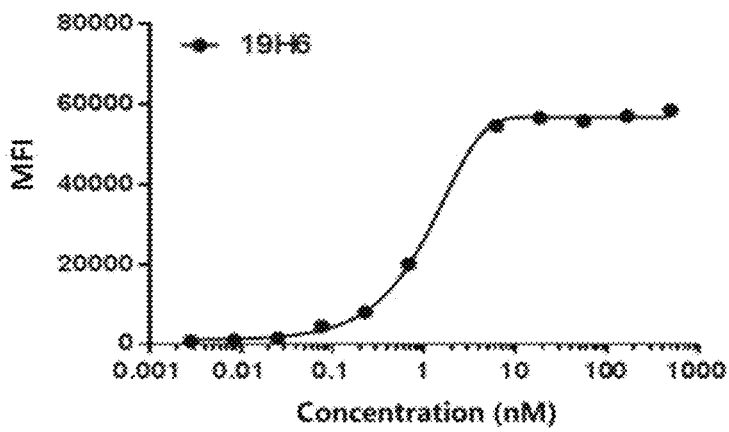
FIG. 4 shows the binding affinity of murine monoclonal antibody 19H6 to breast cancer cells BT474 determined by FACS.

The results are shown in FIG. 4. The results show that 19H6 can specifically bind to breast cancer cells BT474 (with high HER2 expression on the cell surface), with an EC50 of 1.1 nM.

2.3 Determination of Inhibitory Activity of Murine Antibody 19H6 on Target Cell Proliferation In this example, the inhibitory activities of the combination of 19H6 and Herceptin on the proliferation of the target cells with high HER2 expression (breast cancer cells BT474, breast cancer cells SKBR3, gastric cancer cells NCI-N87) were determined.

The experimental method referred to Example 1.2. The 96-well cell culture plate was seeded with 5000 BT474 or NCI-N87 or 3000 SKBR3 cells per well, and the antibody to be tested was directly diluted with cell complete medium in a 3-fold gradient, with the highest working concentration of 10 μg/mL, which was used as the single administration group. The other antibodies to be tested were diluted in complete cell culture medium in a 3-fold gradient with 1 μg/mL Herceptin (final concentration), which was used as a combined administration group of Herceptin.

Figure 5:
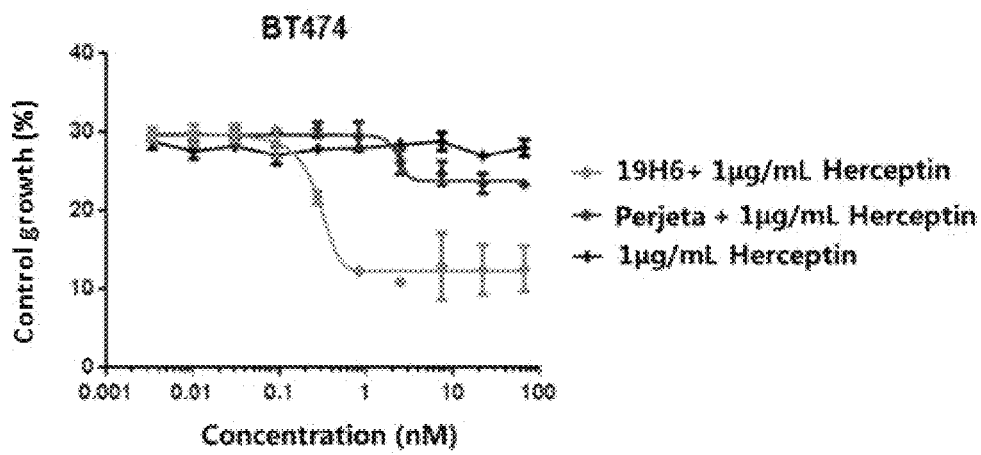
FIG. 5 shows the proliferation inhibition results of the combination of murine monoclonal antibody 19H6 and Herceptin on breast cancer cells BT474.

The results are shown in FIG. 5. The combination of 19H6 and 1 μg/mL of Herceptin can effectively inhibit the proliferation of breast cancer cells BT474, and its inhibitory effect is significantly better than that of the combination of Perjeta and Herceptin or Herceptin as a single agent. The maximum inhibitory effect is more than twice the effect of the combination of Perjeta and Herceptin or Herceptin as a single agent.

Figure 6:
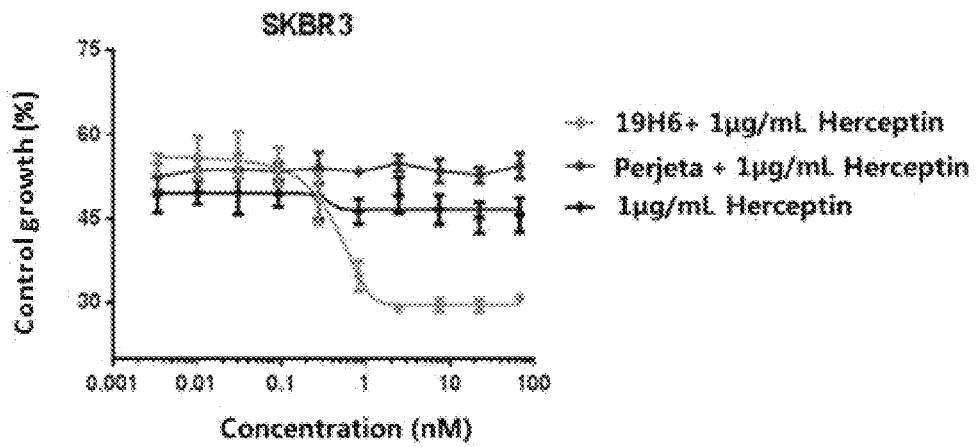
FIG. 6 shows the proliferation inhibition results of the combination of murine antibody 19H6 and Herceptin on breast cancer cells SKBR3.

The results are shown in FIG. 6. The combination of 19H6 and 1 μg/mL Herceptin can effectively inhibit the proliferation of breast cancer cells SKBR3, and its inhibitory effect is significantly better than that of the combination of Perjeta and Herceptin or Herceptin as a single agent. The maximum inhibitory effect is more than 1.5 times the effect of the combination of Perjeta and Herceptin or Herceptin as a single agent.

Figure 7:
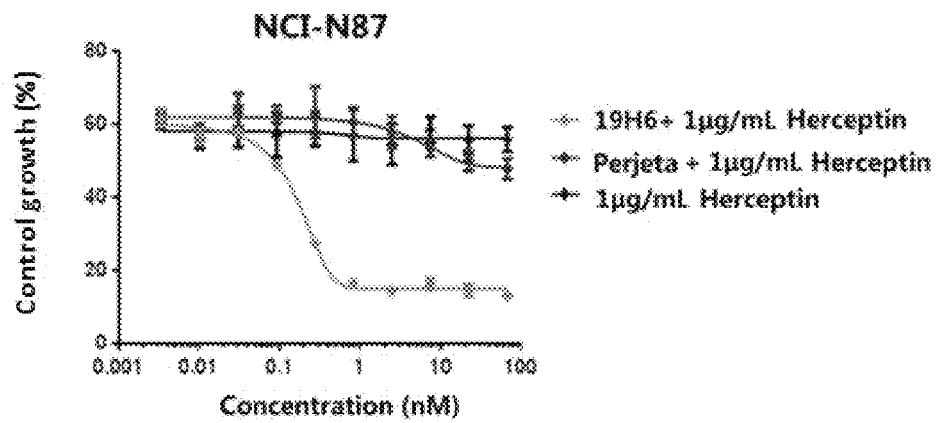
FIG. 7 shows the proliferation inhibition results of the combination of murine antibody 19H6 and Herceptin on gastric cancer cells NCI-N87.

The results are shown in FIG. 7. The combination of 19H6 and 1 μg/mL Herceptin can effectively inhibit the proliferation of gastric cancer cells NCI-N87, and its inhibitory effect is significantly better than that of the combination of Perjeta and Herceptin or Herceptin as a single agent. The maximum inhibitory effect is about 4 times the effect of the combination of Perjeta and Herceptin, and 4.5 times the effect of Herceptin as a single agent.

Example 3 Determination of Antigen Binding Epitope of Murine Anti-Human HER2 Monoclonal Antibody 19H6

3.1 Determination of Competition Between Murine Antibody 19H6 and Herceptin as Well as Perjeta in Binding to Antigen Epitope In this example, the binding epitope relationship of 19H6, Herceptin and Perjeta to human HER2-ECD was determined by competitive ELISA.

Each of 19H6, Perjeta and Herceptin was labeled with biotin, which was performed using NHS activated biotin (Cat #H1759) from Sigma according to the instructions. NHS activated biotin was dissolved in DMSO to a final concentration of 10 mg/mL. 1 mg (1 mL) each of 19H6, Perjeta and Herceptin was mixed well with 50 μg (5 μL) of biotin, after 2 h at room temperature, 100 μL of Tris buffer (1 M, pH 8.0) was added; dialyzed overnight at 4° C. in a large volume of PBS (pH 7.2) for use.

The human HER2-ECD was diluted to 1 μg/mL with the coating solution, and used to coat the ELISA plate, 100 μL/well, incubated overnight at 4° C.; the plate was washed 3 times with PBST, added with 2% BSA-PBS at 200 μL/well, blocked at 37° C. for 1h; each of 19H6, Perjeta, Herceptin was diluted gradually, and each of the biotinylated 19H6, Perjeta, Herceptin was diluted to 10 ng/ml. The serial dilution samples of 19H6, Perjeta, Herceptin were mixed with the diluted biotinylated 19H6, Perjeta, and Herceptin at a volume ratio of 1:1, respectively. Meanwhile, the serial dilution samples of 19H6, Perjeta, Herceptin were mixed with the diluent (1% BSA-PBST) at a volume ratio of 1:1, respectively, as a blank control. Each of the above mixture was added to the ELISA plate at 100 μL/well, incubated at 37° C. for 1 h. After washing 3 times with PBST, HRP-labeled streptavidin (SA, streptavidin, Sigma, Cat #S4672-5 MG) (diluted according to the instructions) was added at 100 μL/well, and incubated at 37° C. for 30 min. After washing 5 times with PBST, TMB was added at 100 μL/well, reacted at room temperature in the dark for 5 min, and then 50 μL/well of 2M $H_2SO_4$ was added. The absorbance OD450 was measured with a microplate reader at 450 nm wavelength.

Figure 8A:
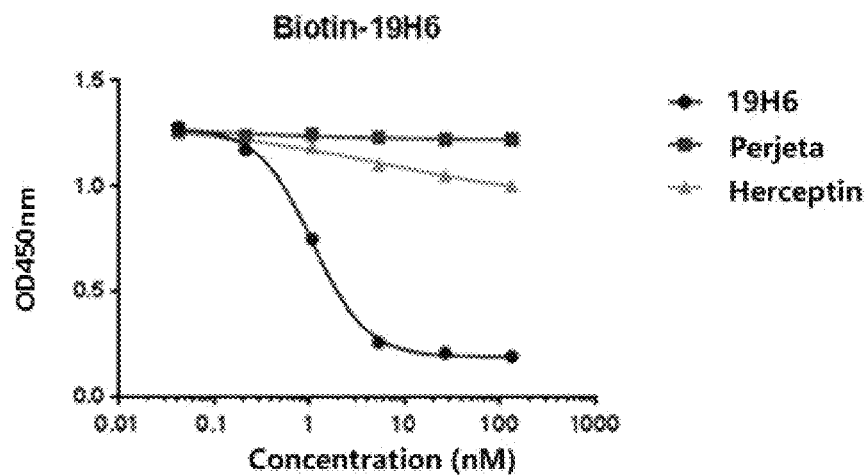
FIG. 8A: serially diluted 19H6/Herceptin/Perjeta were mixed with 10 ng/mL of biotinylated 19H6 at a ratio of 1:1 and then incubated with HER2-ECD.
Figure 8B:
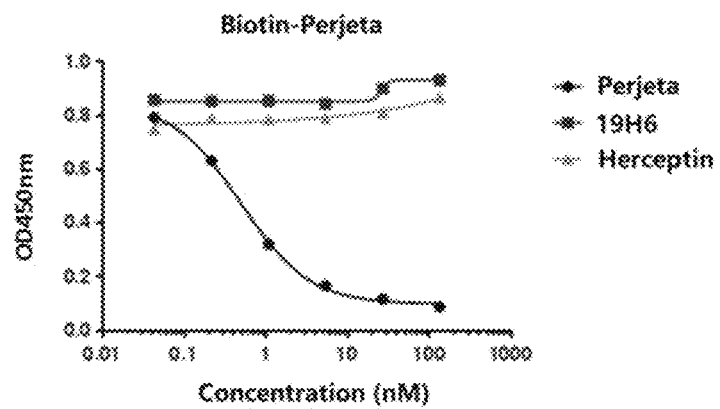
FIG. 8B: serially diluted 19H6/Herceptin/Perjeta were mixed with 10 ng/mL of biotinylated Perjeta at a ratio of 1:1 and then incubated with HER2-ECD.
Figure 8C:
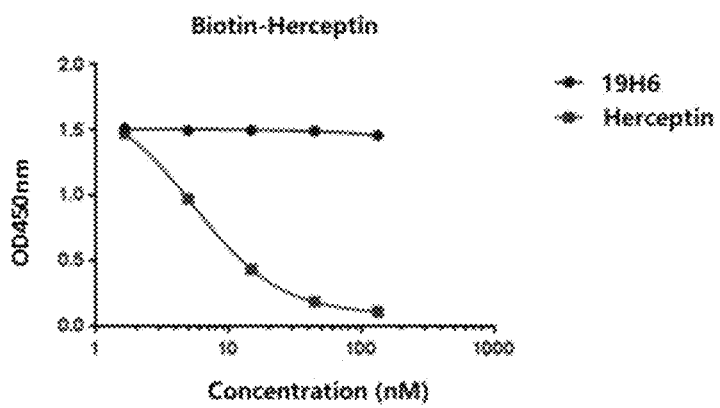
FIG. 8C: serially diluted 19H6/Herceptin/Perjeta were mixed with 10 ng/ml of biotinylated Herceptin at a ratio of 1:1 and then incubated with HER2-ECD.

The results are shown in FIGS. 8A-8C. 19H6 can significantly inhibit the binding of biotinylated 19H6 to human HER2-ECD, while neither Herceptin nor Perjeta can inhibit the binding of biotinylated 19H6 to human HER2-ECD, and 19H6 also cannot inhibit the binding of biotinylated Herceptin or Perjeta to human HER2-ECD, indicating that there is no correlation between 19H6 and the binding epitope of Herceptin/Perjeta to human HER2-ECD, that is, the binding epitope of 19H6 to human HER2-ECD is different from that of Herceptin and perjeta.

3.2 Determination of Binding Ability of Murine Antibody 19H6 with Reduced-Denatured HER2-ECD In this example, the binding ability of 19H6 with reduced-denatured human HER2-ECD was measured by Western Blot.

The reduced-denatured human HER2-ECD was subjected to SDS-PAGE electrophoresis (2 ng/lane), transferred to PVDF membrane by electrotransfer method, blocked in 3% BSA-TBS (37° C., 2 h), and added with 1 μg/ml of 19H6, Herceptin and Perjeta solution (1% BSA-TBST dilution), respectively, incubated at 37° C. for 1 h. After washing 3 times with TBST, HRP-labeled goat anti-mouse IgG secondary antibody (purchased from Millipore, Cat #AP181P, diluted 5000 times with 1% BSA-TBST according to the instructions) or HRP-labeled goat anti-human IgG secondary antibody (purchased from Millipore Company, Cat #AP101P diluted 5000 times with 1% BSA-TBST according to the instructions) was added and incubated at 37° C. for 0.5h. After washing 5 times with TBST, appropriate amount of Immobilon Western Chemiluminescent HRP Substrate solution (purchased from Millipore, Cat #WBKLS0500) was dropwise added on the PVDF membrane, and automatically imaged on a biomolecular imager (purchased from GE, model Las400mini) at room temperature in the dark.

Figure 9:
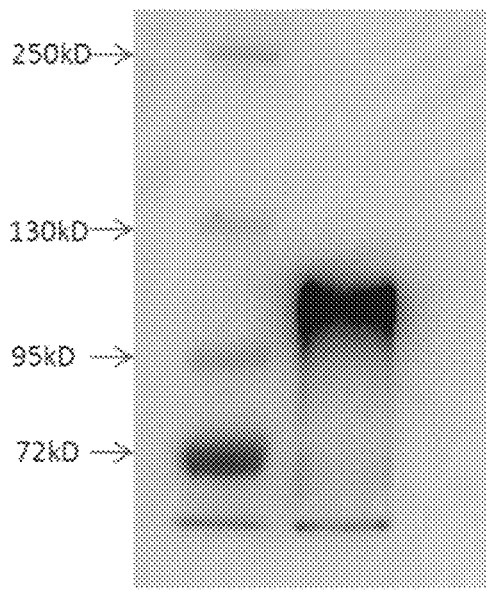
FIG. 9 shows the binding results of murine monoclonal antibody 19H6 to reduced-denatured human HER2-ECD determined by Western blot.

The results are shown in FIG. 9. Specific immunoblotting appeared between the target positions of 95 kD to 130 kD, which shows that 19H6 can specifically bind to the reduced-denatured human HER2-ECD, suggesting that the epitope of human HER2 protein that 19H6 specifically binds to is a linear epitope. In contrast to 19H6, Herceptin and Perjeta did not show the ability to bind to the reduced-denatured human HER2-ECD in the same experiment.

3.3 Determination of Binding Region of Murine Antibody 19H6 to Target Antigen

In this example, the binding region of 19H6 to human HER2-ECD was determined by conventional Western blot and ELISA.

In order to confirm the binding epitope of 19H6 to human HER2, by searching literatures and NCBI, the extracellular domain (HER2-ECD) gene of human HER2 (HER2-ECD) was obtained (amino acids 1 to 652 of NCBI accession number: NP_004439.2, the amino acid sequence is shown in SEQ ID NO: 1, and the nucleotide sequence is shown in SEQ ID NO: 2), wherein, the amino acid sequence shown in SEQ ID NO: 1 comprises the signal peptide sequence SP (1-22), the functional domain I (23-217), the functional domain II (218-342), and the functional domain III (343-510), the functional domain IV (511-582). Then the four functional domains (DI-DIV) of HER2-ECD were combined and expressed, namely HER2-ECD-DI (1-217), HER2-ECD-DI-DII (1-342), HER2-ECD-DI-DIII (1-510) and HER2 extracellular domain full-length protein HER2-ECD-fl (1-652). Subsequently, referring to the methods described in Examples 3.2 and 1.2, the recognition of each domain of human HER2-ECD by 19H6 was determined by conventional Western blot and ELISA, respectively.

Figure 10A:
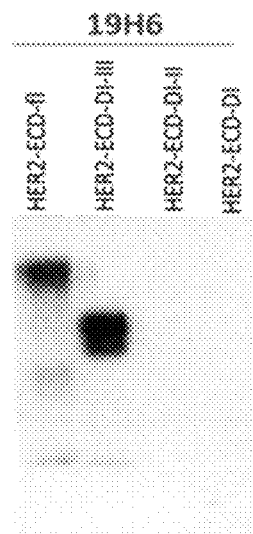
FIG. 10A: detection results of Western blot.
Figure 10B:
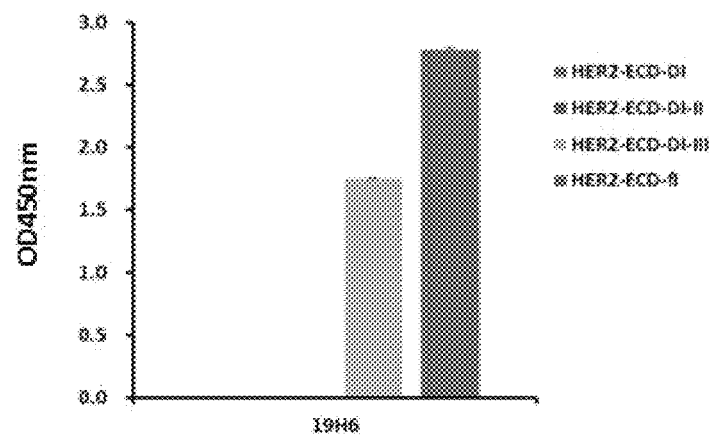
FIG. 10B: detection results of ELISA.

The results are shown in FIG. 10A and FIG. 10B. Both Western blot and ELISA detection results show that the recognition site of 19H6 is located in the third functional domain III (DIII) of human HER2-ECD, which is different from the recognition domains of Herceptin and Perjeta. It is shown through literature review that the recognition domain of Herceptin is DIV, and the recognition domain of Perjeta is DII.

3.4 Confirmation of Key Sites that Affect Binding of Murine Antibody 19H6 to Target Antigen In this example, the binding ability of 19H6 to the polypeptide in the human HER2-ECD DIII region was detected by ELISA, then to further confirm the key sites that affect the binding of 19H6 to human HER2-ECD.

From the results of Examples 3.2 and 3.3, it has been confirmed that 19H6 can bind to denatured HER2-ECD and HER2-ECD DIII. The epitope bound by 19H6 was judged to be a linear epitope. Synthetic polypeptides can be employed and detected by ELISA to further clarify the position of the epitope bound by 19H6.

First, human HER-ECD DIII was decomposed into 6 overlapping parts, and each part synthesized an N-terminal biotin-modified (i.e., bio-) polypeptide, namely:

YC-25: bio-YGLGMEHLREVRAVTSANIQEFAG (343-366);
AA-26: bio-AGCKKIFGSLAFLPESFDGDPASNTA (365-390);
NC-38: bio-NTAPLQPEQLQVFETLEEITGYLYI-SAWPDSLPDLSV (388-424);
LC-41: bio-LSVFQNLQVIRGRILHNGAYSLTLQGL-GISWLGLRSLREL (422-461);
EC-34: bio-ELGSGLALIHHNTHLCFVHTVPWDQL-FRNPHQA (460-492);
HA-21: bio-HQALLHTANRPEDECVGEGLA (490-510).

Figure 11:
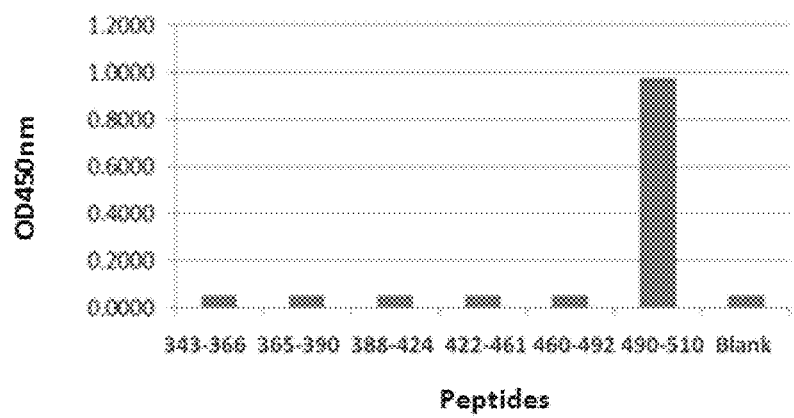
FIG. 11 shows the binding results of murine monoclonal antibody 19H6 to 6 polypeptides in the HER2-ECDDIII region determined by ELISA.

The results are shown in FIG. 11. 19H6 only binds to peptide HA-21, which is the polypeptide of amino acids 490-510 at the N-terminus of the human HER2-ECD protein, indicating that the binding epitope of 19H6 is located between $H_{490}$ and A510 of the human HER2 protein.

Then, the HA-21 polypeptide was further decomposed to synthesize 4 overlapping N-terminal biotin-modified polypeptides, namely:

3-2: bio-DQLFRNPHQALL (483-494);
3-3: bio-QALLHTANRPED (491-502);
3-4: bio-RPEDECVGEGLA (499-510);
3-5: bio-EGLACHQLCARG (507-518).

Figure 12:
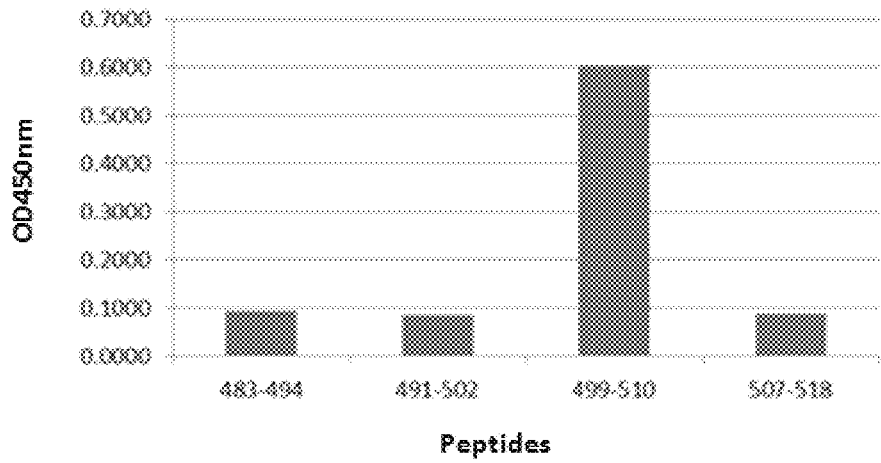
FIG. 12 shows the binding results ofmurine monoclonal antibody 19H6 to 4 polypeptides in the peptide HA-21 region determined by ELISA.

The results are shown in FIG. 12. 19H6 only binds to peptide 3-4, which is the peptide of amino acids 499-510 at the N-terminus of human HER2-ECD protein, indicating that the binding epitope of 19H6 is located between R499 and A510 of the human HER2 protein.

Finally, by the means of alanine scanning (single point mutation of non-alanine amino acid position to alanine, respectively), 12 N-terminal biotin-modified polypeptides (495-510) were synthesized, namely:

4-1: bio-ATANRPEDECVGEGLA;
4-2: bio-HAANRPEDECVGEGLA;
4-3: bio-HTAARPEDECVGEGLA;
4-4: bio-HTANAPEDECVGEGLA;
4-5: bio-HTANRAEDECVGEGLA;
4-6: bio-HTANRPADECVGEGLA;
4-7: bio-HTANRPEAECVGEGLA;
4-8: bio-HTANRPEDACVGEGLA;
4-9: bio-HTANRPEDEAVGEGLA;
4-10: bio-HTANRPEDECAGEGLA;
4-11: bio-HTANRPEDECVGAGLA;
4-12: bio-HTANRPEDECVGEGAA.

Figure 13:
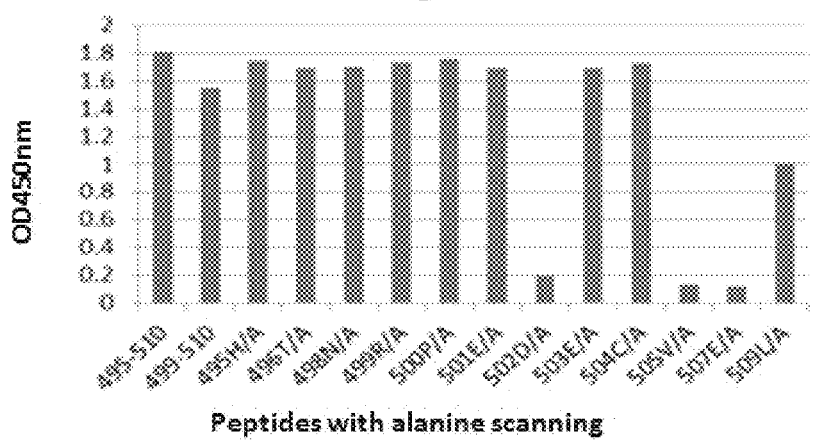
FIG. 13 shows the binding results of murine monoclonal antibody 19H6 to 12 polypeptides from alanine scanning mutagenesis determined by ELISA.

The results are shown in FIG. 13. 19H6 basically has no binding ability with peptide 4-7 (D502A), peptide 4-10 (V505A), peptide 4-11 (E507A), and the binding to peptide 4-12 (L509A) is also weaker than other polypeptides. Accordingly, it is preliminarily determined that the core key amino acid sites that affect the binding of 19H6 to human HER2-ECD are D502, V505, E507, and L509 is the less important amino acid site.

3.5 Further Confirmation of Key Sites of Murine Antibody 19H6 Binding to Target Antigen In this example, the binding ability of 19H6 and human HER2-ECD site-directed mutant protein was detected by ELISA.

The HER2-ECD-His-pTT5 expression vector was subjected to site-directed mutation by PCR (polymerase chain reaction), that is, the aspartic acid at position 502 was mutated into alanine (HER2-ECD-D502A), the valine at position 505 was mutated into alanine (HER2-ECD-V505A) and the glutamic acid at position 507 was mutated into alanine (HER2-ECD-E507A). Meanwhile, an expression vector comprising double points mutation of aspartic acid at position 502 and valine at position 505 (HER2-ECD-D502A/V505A), and a three-point mutation of aspartic acid at position 502, valine at position 505 and glutamic acid at position 507 (HER2-ECD-D502A/V505A/E507A) was constructed. After the above-mentioned vectors were verified by sequencing, they were transfected into HEK293E (purchased from NRC biotechnology Research Institute) for expression, and 5 days after transfection, the expression supernatant was collected and purified for use. The above purified HER2-ECD protein and each mutant protein were subjected to 19H6 binding affinity determination with reference to the description in Example 1.2.

Figure 14:
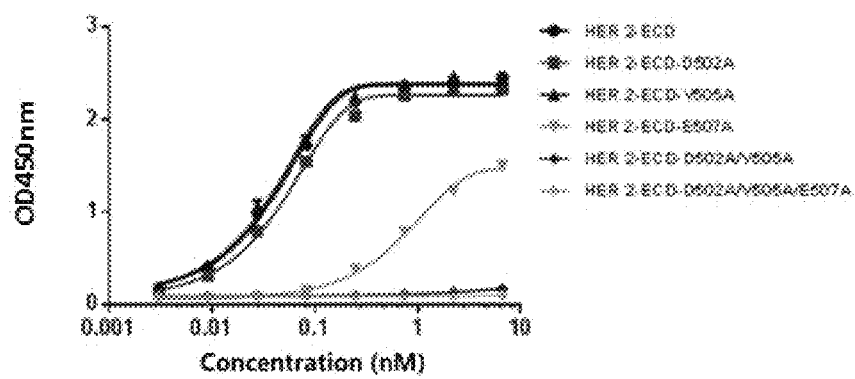
FIG. 14 shows the binding results of 19H6 to various site-directed mutated human HER2-ECD proteins determined by ELISA.

The results are shown in FIG. 14. The EC50 of 19H6 targeting HER2-ECD, HER2-ECD-D502A, HER2-ECD-E505A and HER2-ECD-E507A were 0.041 nM, 0.05 nM, 0.038 nM and 0.867 nM, respectively, but it had almost no binding effect to HER2-ECD-D502A/V505A and HER2-ECD-D502A/V505A/E507A. This further illustrates the importance of the three-point mutations of aspartic acid at position 502, valine at position 505 and glutamic acid at position 507 of HER2-ECD for the targeted binding of 19H6 to HER2-ECD. Among them, single-point mutation, especially glutamate at position 507, has the most significant impact. Similarly, we performed related binding epitope determination experiments on the subsequent humanized antibody 19H6-Hu and obtained the same results.

Example 4 Preparation and Activity Identification of Chimeric Antibody of Murine Anti-Human HER2 Monoclonal Antibody 19H6

4.1 Preparation of Chimeric Antibody 19H6-Ch

In this example, the heavy chain variable region and the light chain variable region of 19H6 were obtained by the methods related to molecular biology, and the chimeric antibody 19H6-ch was further constructed.

The RNA of 19H6 hybridoma cells was extracted by Trizol and subjected to mRNA reverse transcription to obtain cDNA. Then, using the cDNA as a template, the heavy and light chain degenerate primers of the murine antibody (Antibody Engineering, Volume 1, Edited by Roland Kontermann and Stefan Dübel, the sequence of the combined primers is from page 323) were used to perform PCR, respectively. The obtained PCR product (about 700 bp) were sequenced and analyzed through the kabat database to confirm that the obtained sequence was the variable region sequence of the murine antibody. The sequence information is as follows: the heavy chain variable region gene sequence is 351 bp, encoding 117 amino acid residues, the amino acid sequence is shown in SEQ ID NO: 3, the nucleotide sequence is shown in SEQ ID NO: 4; the light chain variable region gene sequence is 336 bp, encoding 112 amino acid residues, the amino acid sequence is shown in SEQ ID NO: 5, the nucleotide sequence is shown in SEQ ID NO: 6.

The obtained heavy chain variable region sequence was spliced with human IgG1 constant region (having the amino acid sequence as shown in SEQ ID NO: 7 and the nucleotide sequence as shown in SEQ ID NO: 8), and the light chain variable region sequence was spliced with the constant region of human kappa chain (having the amino acid sequence as shown in SEQ ID NO: 9 and the nucleotide sequence as shown in SEQ ID NO: 10), the heavy chain and light chain of 19H6-ch were constructed into the pTT5 expression vector, and transfected into HEK-293E cells, purified to obtain chimeric antibody 19H6-ch. SDS-PAGE electrophoresis was used to determine whether the molecular weight of the expressed antibody is correct and detect the purity of the antibody. Then the antibody was quantified, packed, and frozen at −80° C. for use.

Figure 15:
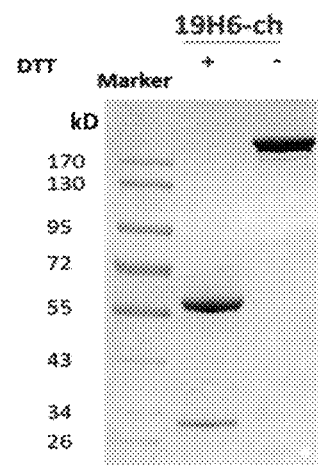
FIG. 15 shows the SDS-PAGE electrophoresis results of chimeric antibody 19H6-ch.

The results are shown in FIG. 15. The results show that the prepared 19H6-ch has the same molecular weight as expected, with the purity of above 95%.

4.2 Determination of Affinity of Chimeric Antibody 19H6-Ch to Target Antigen

In this example, the affinity of 19H6-ch to human HER2-ECD was determined by ELISA.

The experimental method referred to Example 1.2.

Figure 16:
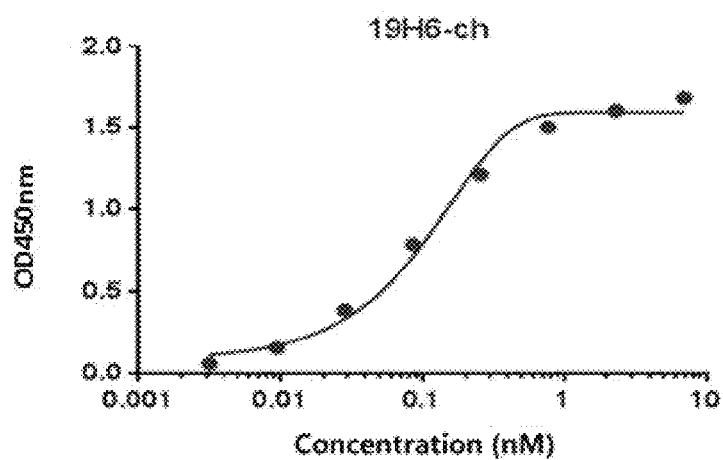
FIG. 16 shows the binding affinity of chimeric antibody 19H6-ch to human HER2-ECD protein determined by ELISA.

The results are shown in FIG. 16, indicating that 19H6-ch has a binding affinity to human HER2-ECD comparable to 19H6, with an EC50 of 0.1 nM.

4.3 Determination of Binding Affinity of Chimeric Antibody 19H6-Ch to Target Cells In this example, the binding affinity of 19H6-ch to breast cancer cells BT474 was determined by the FACS.

The experimental method referred to Example 2.2.

Figure 17:
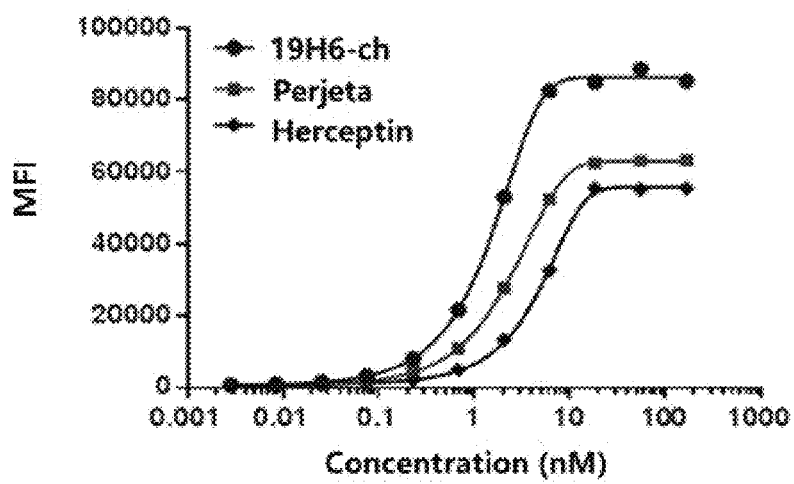
FIG. 17 shows the binding affinity of chimeric antibody 19H6-ch to breast cancer cells BT474 determined by FACS.

The results are shown in FIG. 17, indicating that 19H6-ch can specifically bind to breast cancer cells BT474. It was calculated from the figure that 19H6-ch, Herceptin and Perjeta had an EC50 of 1.5 nM, 4.8 nM and 2.4 nM, respectively, indicating that the binding activity of 19H6-ch to breast cancer cell BT474 is better than the current marketed HER2-targeting drugs Herceptin and Perjeta.

4.4 Determination of Inhibitory Activity of Chimeric Antibody 19H6-Ch on Target Cell Proliferation In this example, the inhibitory activities of the combination of the chimeric antibody 19H6-ch and Herceptin on the proliferation of the target cells with high HER2 expression (breast cancer cells BT474, breast cancer cells SKBR3, gastric cancer cells NCI-N87) were determined.

The experimental method referred to Example 2.3.

Figure 18:
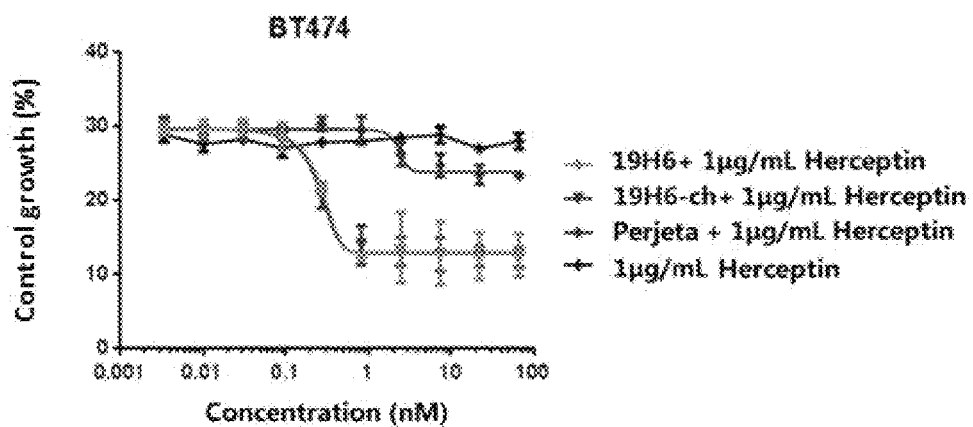
FIG. 18 shows the proliferation inhibition results of chimeric antibody 19H6-ch combination with Herceptin on breast cancer cells BT474.
Figure 19:
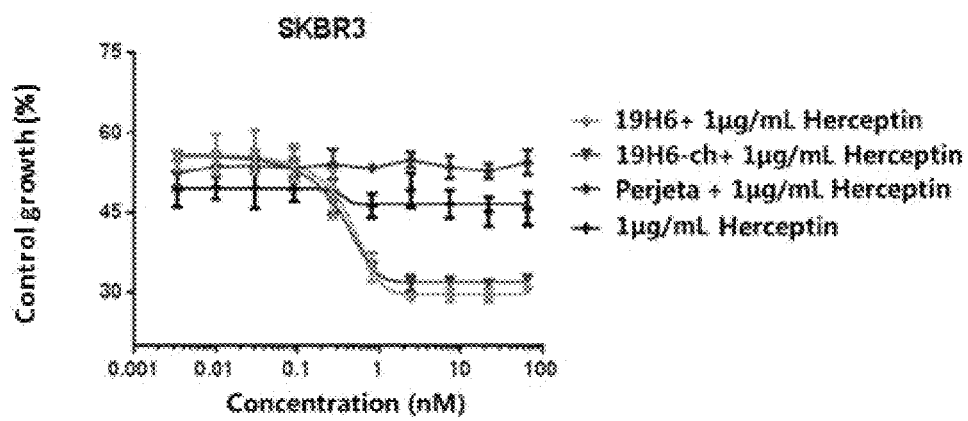
FIG. 19 shows the proliferation inhibition results of chimeric antibody 19H6-ch combination with Herceptin on breast cancer cells SKBR3.
Figure 20:
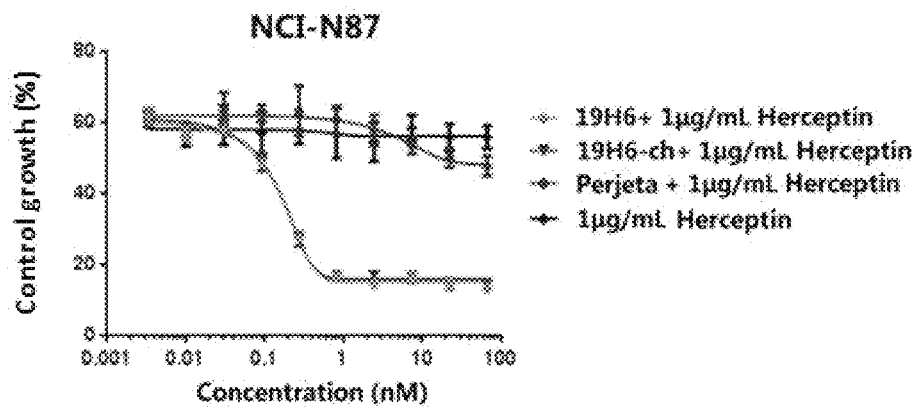
FIG. 20 shows the proliferation inhibition results of chimeric antibody 19H6-ch combination with Herceptin on gastric cancer cells NCI-N87.

The results are shown in FIG. 18, FIG. 19 and FIG. 20, respectively. The results show that the combination of 19H6-ch and 1 μg/mL of Herceptin can effectively inhibit the proliferation of breast cancer cells BT474, SKBR3 and gastric cancer cells NCI-N87, and has a significantly better inhibitory effect than the combination of Perjeta and Herceptin or Herceptin as single agent. Its inhibitory activities on the proliferation of these three tumor cells are consistent with 19H6.

Example 5 Preparation and Activity Identification of Humanized Antibody of Murine Anti-Human HER2 Monoclonal Antibody 19H6

5.1 Preparation of Humanized Antibodies 19H6-Hu and 19H6-Graft

By analyzing the amino acid sequences of the light chain variable region and the heavy chain variable region,3 antigen complementarity determining regions (CDR) and 4 framework regions (FR) of the murine antibody 19H6 were determined according to the Kabat rule. Wherein, the amino acid sequence of the heavy chain complementarity determining region comprises HCDR1: DYAIH (SEQ ID NO: 11), HCDR2: VFSIYYENINYNQKFKG (SEQ ID NO: 12) and HCDR3: RDGGTINY (SEQ ID NO: 13), and the amino acid sequence of the light chain complementarity determining region comprises LCDR1: RSSQSLVHSNGNTYLH (SEQ ID NO: 14), LCDR2: KVSNRFS (SEQ ID NO: 15) and LCDR3: SQSTHIPWT (SEQ ID NO: 16).

The humanized template that best matches the 19H6 non-CDR region was selected in the Germline database. Then the CDR region of 19H6 was transplanted to the selected humanized template to replace the CDR region of the human template, and recombined with the IgGI constant region. Meanwhile, based on the three-dimensional structure of the antibody, the embedded residues, the residues that directly interact with CDR region, and the residues that have an important impact on the conformation of VL and VH of 19H6 were back-mutated, finally two humanized antibodies were selected, i.e. 19H6-Hu and 19H6-graft. Wherein, the heavy chain variable region gene sequence of 19H6-graft is 351 bp, encoding 117 amino acid residues, the amino acid sequence is shown in SEQ ID NO: 17, the nucleotide sequence is shown in SEQ ID NO: 18; the light chain variable region gene sequence is 336 bp, encoding 112 amino acid residues, the amino acid sequence is shown in SEQ ID NO: 19, and the nucleotide sequence is shown in SEQ ID NO: 20. The heavy chain variable region gene sequence of 19H6-Hu is 351 bp, encoding 117 amino acid residues, the amino acid sequence is shown in SEQ ID NO: 21, the nucleotide sequence is shown in SEQ ID NO: 22; the light chain variable region gene sequence is 336 bp, encoding 112 amino acid residues, the amino acid sequence is shown in SEQ ID NO: 23, and the nucleotide sequence is shown in SEQ ID NO: 24. The same constant region as that of 19H6-ch was used to construct the heavy and light chains of 19H6-Hu and 19H6-graft into pTT5 expression vector, respectively, which were transfected into HEK-293E cells, and purified to obtain humanized antibodies 19H6-Hu and 19H6-graft. SDS-PAGE electrophoresis was used to determine whether the molecular weight of the expressed antibody is correct and detect the purity. Then the antibodies were quantified, packed, and frozen at −80° C. for use.

Figure 21A:
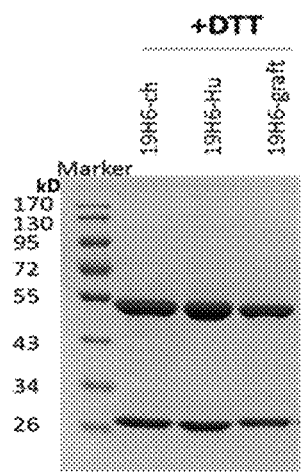
FIG. 21A: the results of reduction electrophoresis with DTT.
Figure 21B:
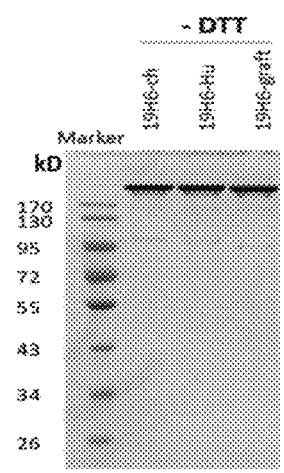
FIG. 21B: the results of non-reduction electrophoresis without DTT.

The results are shown in FIG. 21A and FIG. 21B. The results show that the prepared 19H6-Hu and 19H6-graft have the same molecular weights as expected, with the purity of above 95%.

5.2 Determination of Affinity of Humanized Antibodies 19H6-Hu and 19H6-Graft to Target Antigen In this example, the affinity of humanized antibodies 19H6-Hu and 19H6-graft to human HER2-ECD was determined first by ELISA.

The experimental method referred to Example 1.2.

Figure 22:
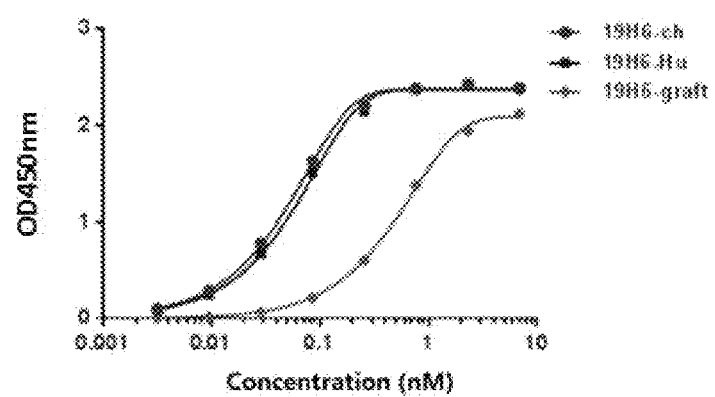
FIG. 22 shows the binding affinity of humanized antibodies 19H6-Hu and 19H6-graft to human HER2-ECD determined by ELISA.

The results are shown in FIG. 22, indicating that the humanized antibody 19H6-Hu has a binding affinity comparable to that of the chimeric antibody 19H6-ch, with EC50 of 0.06 nM and 0.05 nM, respectively, while the binding affinity of 19H6-graft is relatively weak, with an EC50 of 0.5 nM. Therefore, the humanized antibody 19H6-Hu was selected for further research and development.

In addition, the binding kinetics of 19H6-Hu to HER2-ECD was also measured in this example by the biacore method, which was as follows: using the capture method, 0.5 μg/mL of 19H6-Hu antibody was captured by the ProteinA chip (purchased from GE, Lot No.10261132). The procedure was set as follows: contact time 75s, flow rate 10 μL/min, regeneration contact time 30s. The antigen HER2-ECD was used as the analyte, and the procedure was set as follows:

contact time 180s, dissociation time 900s, flow rate 30 µL/min, regeneration contact time 30s. The analysis parameters are shown in Table 1.

TABLE 1

Biacoremeasurement results

| Sample name | ka (1/Ms) | kd (1/s) | KD (M) |
|---|---|---|---|
| 19H6-Hu | 1.55E+05 | 1.11E−04 | 7.13E−10 |

5.3 Determination of Binding Affinity of Humanized Antibody 19H6-Hu to Target Cells In this example, the binding affinity of the humanized antibody 19H6-Hu to breast cancer cells BT474 was determined by FACS.

The experimental method referred to Example 2.2.

Figure 23:
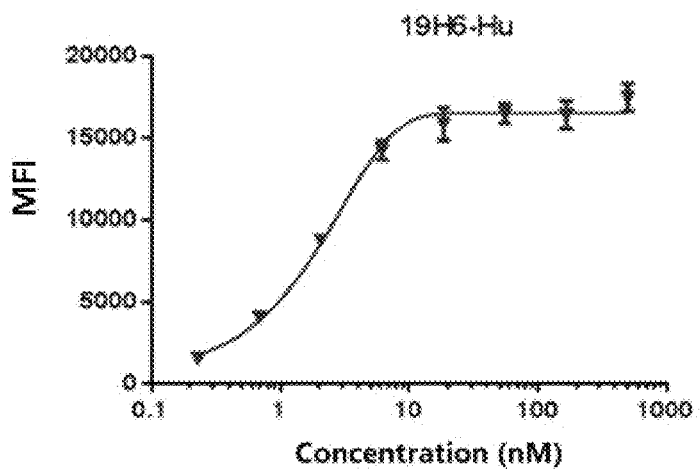
FIG. 23 shows the binding affinity of the humanized antibodies 19H6-Hu to breast cancer cells BT474 determined by FACS.

The results are shown in FIG. 23. The results indicate that 19H6-Hu can specifically bind to breast cancer cells BT474, with an EC50 of 1.9 nM, which is comparable to the activity of 19H6-ch.

5.4 Determination of inhibitory activity of humanized antibody 19H6-Hu on target cell proliferation In this example, the inhibitory activities of the combination of the humanized antibody 19H6-Hu and Herceptin on the proliferation of target cells with high HER2 expression (breast cancer cells BT474, breast cancer cells SKBR3, gastric cancer cells NCI-N87) were determined. The experimental method referred to Example 2.3.

Figure 24:
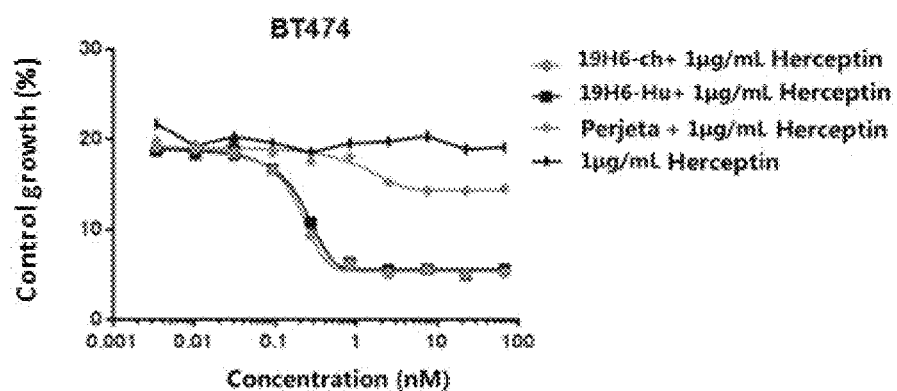
FIG. 24 shows the proliferation inhibition results of humanized antibodies 19H6-Hu combination with Herceptin on breast cancer cells BT474.
Figure 25:
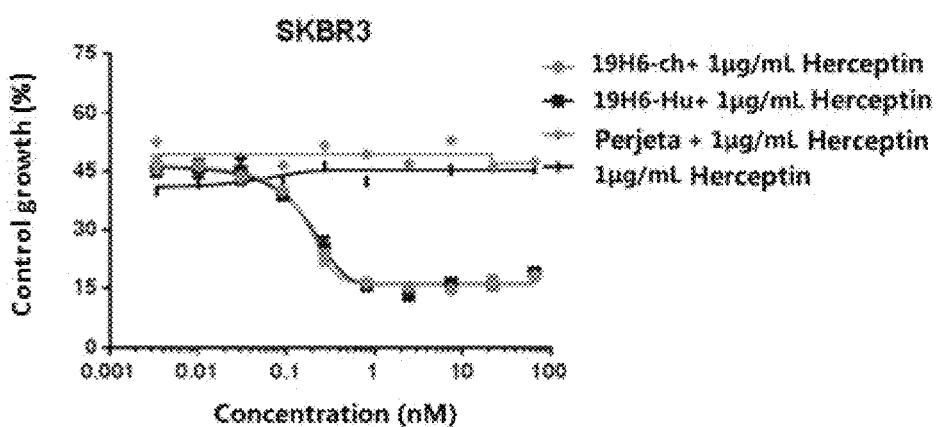
FIG. 25 shows the proliferation inhibition results of humanized antibodies 19H6-Hu combination with Herceptin on breast cancer cells SKBR3.
Figure 26:
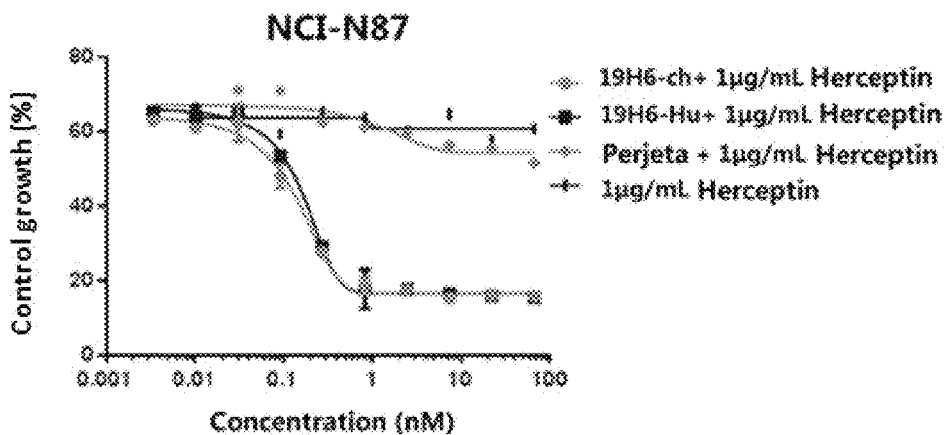
FIG. 26 shows the proliferation inhibition results of humanized antibodies 19H6-Hu combination with Herceptin on gastric cancer cells NCI-N87.

The results are shown in FIG. 24, FIG. 25 and FIG. 26. The results show that the combination of 19H6-Hu and 1 µg/mL of Herceptin can effectively inhibit the proliferation of breast cancer cells BT474, SKBR3 and gastric cancer cells NCI-N87, and has a significantly better inhibitory effect than the combination of Perjeta and Herceptin or Herceptin as single agent. Its inhibitory activities on the proliferation of these three tumor cells are consistent with 19H6-ch, and both of them significantly improve the maximum inhibitory effect of Herceptin as a single agent.

Example 6 Determination of Cross-Species Reaction of Humanized Antibody 19H6-Hu

In this example, the cross-species reaction of the humanized antibody 19H6-Hu was measured by ELISA.

The HER2-ECD proteins of cynomolgus monkey and rat (both purchased from Sino Biological Company, Cat. Nos: 90295-C08H-50 and 80079-R08H-50, respectively), i.e., Cyno-HER2-ECD and Rat-HER2-ECD, were coated on a 96-well ELISA plate at 0.2 µg/well. The cross-reactivity of 19H6-Hu to HER2 of these two species was determined. Other specific experimental methods referred to Example 1.2.

Figure 27:
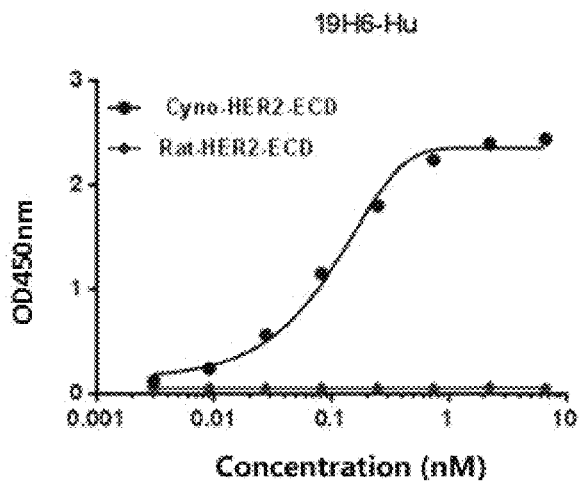
FIG. 27 shows the binding affinity of humanized antibody 19H6-Hu to HER2-ECD protein of different species determined by ELISA.

The results are shown in FIG. 27, indicating that the humanized antibody 19H6-Hu can well recognize the HER2 protein of cynomolgus monkey, with an ECso of 0.1 nM, but cannot recognize the HER2 protein of rat.

Example 7 Determination of selectivity of humanized antibody 19H6-Hu to family members HER1, HER3 and HER4

In this example, the humanized antibody 19H6-Hu's selectivity to family members HER1, HER3 and HER4 was determined by ELISA.

A 96-well ELISA plate was coated with human HER1, HER3 and HER4 proteins (all purchased from Sino Biological Company, Cat. Nos: 10001-$H_{08}$H-20, 10201-$H_{08}$H-20 and 10363-$H_{08}$H-50, respectively) at 0.2 µg/well. The selectivity of 19H6-Hu to HER2 family proteins was determined. Refer to Example 1.2 for other specific experimental methods.

Figure 28:
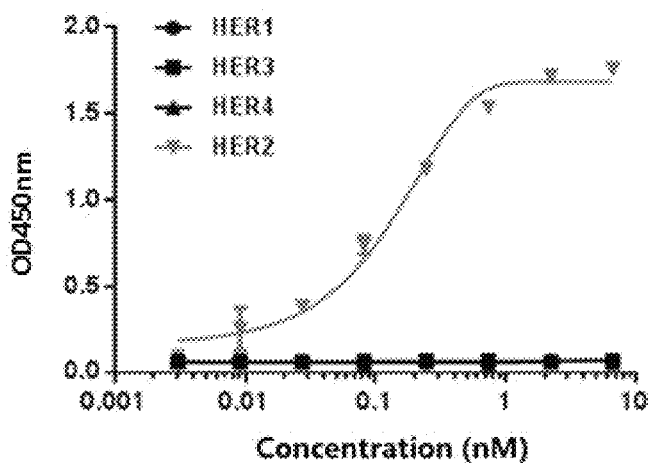
FIG. 28 shows the binding activity of humanized antibody 19H6-Hu to family members HER1, HER3 and HER4 determined by ELISA.

The results are shown in FIG. 28, indicating that 19H6-Hu has no cross-reactivity to HER1, HER3, and HER4, which further shows that 19H6-Hu inhibits the growth of the tumor cells with high HER2 expression by recognizing HER2 specifically.

Example 8 Study of mechanism of humanized antibody 19H6-Hu on tumor cells

In this example, Western blot was used to determine the effect of 19H6-Hu on the downstream related signal pathways of HER2 and the inhibitory effect on HER2/HER3 dimerization.

Breast cancer cells BT474, SKBR3 or gastric cancer cells NCI-N87 in logarithmic growth phase were trypsinized and resuspended in complete medium, plated in a 12-well plate at a plating density of 50% and cultured in a $CO_2$ cell incubator at 37° C. overnight. After the cells adhered to the wall on the next day, the drug was diluted to a specific concentration with the medium containing 1% fetal bovine serum (see Table 2). The medium in the 12-well plate was removed, and 2 mL of sterile PBS at room temperature was gently added to each well to wash away the remaining medium. The PBS was removed, 1 mL of previously prepared various drugs were slowly added to each well, and then the 12 well plate was gently shaken, and cultured in the incubator. After treatment for 24 h, the 12-well plate was placed on ice, the medium was removed, and each well was washed once by gently adding 2 mL of sterile, ice-cold PBS. PBS was removed, 200 µL 1×LDS (NuPAGE LDS Sample Buffer, Thermo Fisher, Cat #NP0008) was added to each well, mixed well and allowed to stand for lysis for several minutes. The LDS cell lysate in the well plate was collected into a centrifuge tube, β-mercaptoethanol was added at a concentration of v: v=5%, mixed well and frozen immediately in−80° C. refrigerator for later use or for detecting the changes of the following biomarkers using conventional Western blot. The sources of each detection antibody were as follows: GAPDH (Cell Signal Technology, Cat #5174); p44/42 MAPK (t-ERK1/2) (Cell Signal Technology, Cat #4695); phospho p44/42 MAPK (p-ERK1/2) (Thr202/Tyr204) (Cell Signal Technology, Cat #4376); AKT (t-AKT) (Cell Signal Technology, Cat #4691); phosphoAKT (p-AKT S473) (Cell Signal Technology, Cat #4060); HER2 (t-HER2) (Cell Signal Technology, Cat #2165), phospho-HER2 (p-HER2 Y1248) (Cell Signal Technology, Cat #2247), HER3 (t-HER3) (Cell Signal Technology, Cat #12708); phospho-HER3 (p-HER3 Y1289) (Cell Signal Technology, Cat #2842), HRP goat anti-rabbit IgG (Beijing Boaolong Immunological Technology Co., Ltd., Cat #BF03008).

TABLE 2

| Plate layout | | | |
|---|---|---|---|
| 19H6-Hu_20 µg/mL | 19H6-Hu_5 µg/mL | 19H6-Hu_1 µg/mL | 19H6-Hu_5 µg/mL + Tras_5 µg/mL |
| Tras_20 µg/mL | Tras_5 µg/mL | Tras_1 µg/mL | Pert_5 µg/mL + Tras_5 µg/mL |
| Pert_20 µg/mL | Pert_5 µg/mL | Pert_1 µg/mL | NC |

Tras: Herceptin;
Pert: Perjeta;
NC: Negative control, without any antibody treatment.

Figure 29:
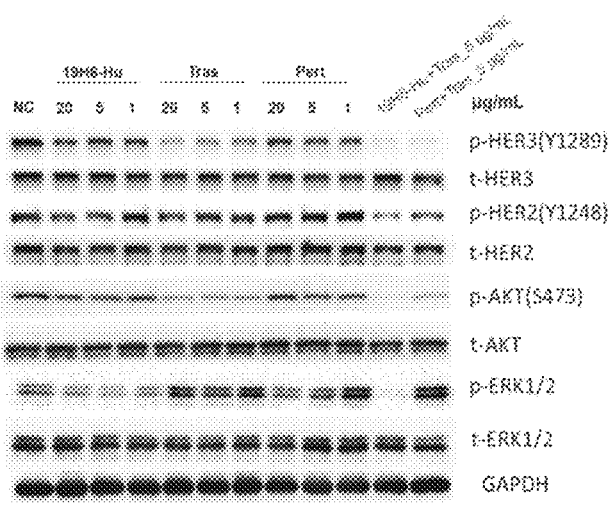
Figure 30:
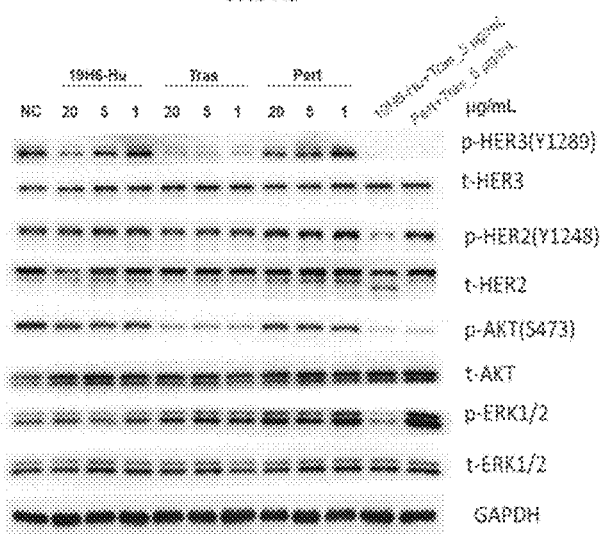
Figure 31:
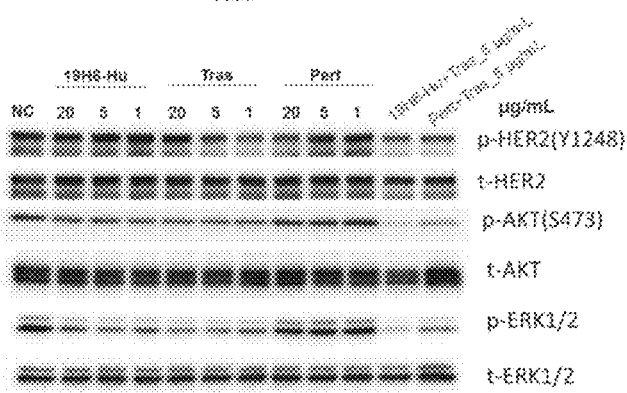

The results are shown in FIG. 29, FIG. 30 and FIG. 31, respectively. Compared with the NC control group, Herceptin as a single agent can significantly inhibit p-HER3 (Y1289) in a dose-dependent manner. And only Herceptin as a single agent can inhibit the phosphorylation of p-AKT (S473) in a dose-dependent manner, but can not inhibit p-HER2 (Y1248). But the combination of 19H6-Hu and Heceptin can significantly inhibit the phosphorylation signals of p-HER3 (Y1289), p-HER2 (Y1248), p-AKT (S473) and p-ERK1/2 and the expression of t-HER2, while the combination of Perjeta and Heceptin only cause the inbition of p-HER3 (Y1289) and p-AKT (S473), and the combination of 19H6-Hu and Heceptin has a significant better inhibitory effect on p-AKT (S473) and p-ERK1/2 than the combination of Perjeta and Heceptin.

In order to further elucidate the mechanism of 19H6-Hu, the inhibitory effect of 19H6-Hu on HER2/HER3 dimerization was studied at BT474 and SKBR3 cells.

BT474 and SKBR3 cells in the logarithmic growth phase were trypsinized and resuspended, and the cells were plated in a 12-well plate at a plating density of 50%, cultured in an incubator overnight to allow the cells to adhere to the wall. On the next day, the drug was gradually diluted with serum-free medium containing 1% fetal bovine serum to a specific concentration, as shown in Table 3. The medium in the 12-well plate was removed, and 2 mL of sterile PBS at room temperature was gently added to each well to wash away the remaining medium. PBS was removed, each well was slowly added with 1 mL of previously prepared various drugs or serum-free medium. The 12 well plate was gently shaken, and cultured in the incubator. After treatment for 2 h, NC wells were filled with 1 mL serum-free medium, and the other wells were added with 1 mL of 4 nM HRG (Heregulin, neuromodulin, purchased from R&D, Cat #396-HB-050) that was previously prepared with serum-free medium, to allow the final concentration of HRG to be 2 nM. After acting for 15 min in the incubator, the 12-well plate was placed on ice, the culture solution was removed from each well, and washed once by gently adding 2 mL of sterile, ice-cold PBS. PBS was removed and 400 μL of pre-cooled IP cell lysate (purchased from Beyotime, Cat #P0013) was added to each well and mixed well for lysis on ice for 5-10 min. After the cell lysis was completed by observing under a microscope, the lysate was collected, centrifuged at 12,000 rpm, 4° C. for 5 min. The supernatants were collected into clean EP tubes and incubated with 100 mM Herceptin at 4° C. for 1h, respectively, and then 20 μL of Protein A/G PLUS-Agarose which was blocked overnight with 5% BSA was added to each tube (beads, purchased from Santa cruz biotechnology, Cat #sc-2003), making up to the final volume of 800 μL with IP cell lysate, and incubated overnight at 4° C. On the next day, the samples were taken out and centrifuged at 2,000 rpm at 4° C. for 6 min, the supernatant was discarded; the beads were collected and washed twice with pre-cooled PBS. 80 μL of 1×LDS (purchased from Invitrogen, Cat #NP0008) was added to each sample, and β-mercaptoethanol was added at a concentration of v: v=5%, flicked and mixed well, and heated at 100° C. for 10 min to remove the protein bound to the beads, and then slightly cooled, centrifuged at 12,000 rmp for 5 min, and ready for sample loading. The biomarkers were detected by conventional Western blot.

TABLE 3

Plate layout

| | | |
|---|---|---|
| NC1: no mAb, no HRG | 19H6-Hu_100 nM | 19H6-Hu_50 nM + Tras_50 nM |
| PC1: only HRG | Tras_100 nM | Tras_50 nM + Pert_50 nM |
| NC2: no mAb, no HRG | Pert_100 nM | PC2: only HRG |

Figure 32:
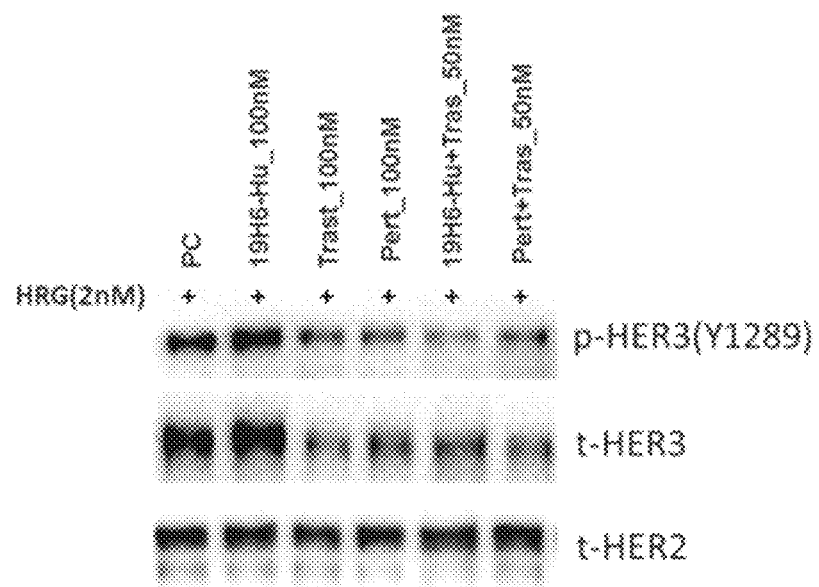
FIG. 32 shows the inhibitory effect of 19H6-Hu on HER2/HER3 dimerization in BT474 cells.
Figure 33:
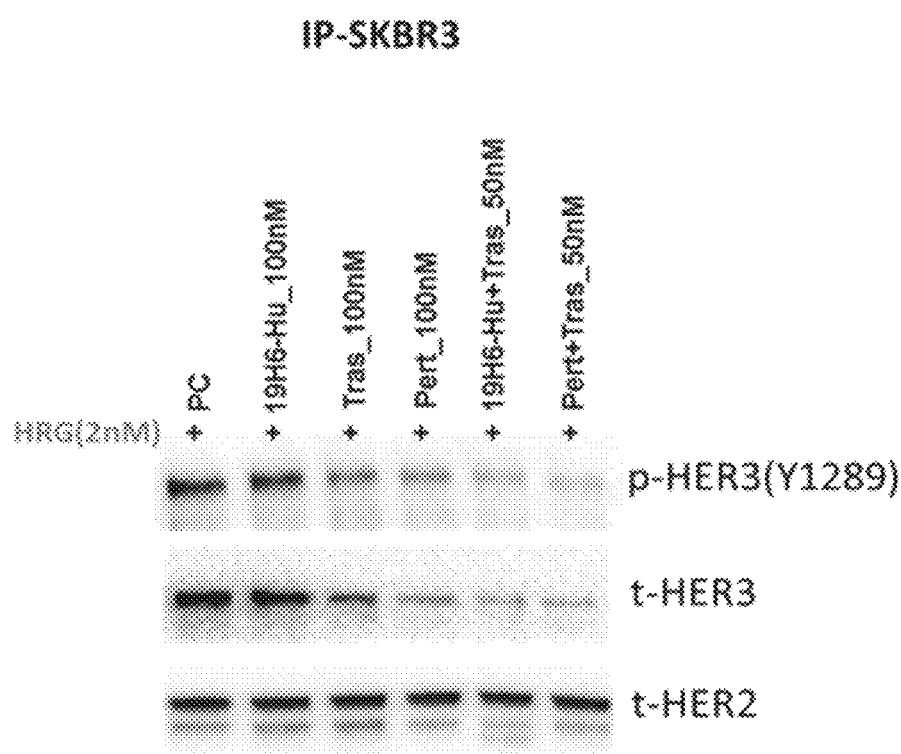
FIG. 33 shows the inhibitory effect of 19H6-Hu on HER2/HER3 dimerization in SKBR3 cells.

The results are shown in FIG. 32 and FIG. 33, respectively. It was observed on both SKBR3 and BT474 cell lines that, when 19H6-Hu was used as a single agent, there was no significant change of the amount of p-HER3 (Y1289) and t-HER3 co-immunoprecipitated by HER2 in comparison with the positive control group (PC), while Perjeta significantly down-regulated the amount of p-HER3 (Y1289) and t-HER3. Herceptin only had a weak regulation effect. This indicates that 19H6-Hu has a different mechanism of action from Perjeta, which can significantly inhibit the dimerization of HER2/HER3. But the combination of 19H6-Hu and Herceptin has an equivalent effect on the inhibition of HER2/HER3 dimerization to Perjeta as a single agent and its combination with Herceptin.

Example 9 Determination of in Vivo Pharmacodynamic Activity of Humanized Antibody 19H6-Hu In this example, the anti-tumor effects of the combination of 19H6-Hu and Herceptin in NCI-N87 and HCC1954 xenograft tumor models were determined, respectively.

Experimental BALB/c nude mice, female, 40-45 days old, weighing 18-20 g, were purchased from Shanghai Lingchang Biotechnology Co., Ltd.

NCI-N87 and HCC1954 cells in the logarithmic growth phase were collected, adjusted to a cell concentration of $16 \times 10^7$/mL and resuspended in a serum-free medium, and mixed with matrigel at a ratio of 1:1. Under aseptic conditions, 100 μL of the cell suspension was inoculated under the skin of the back of nude mice, i.e. $8 \times 10^6$/mouse. The length and width of the xenograft tumors were measured with a vernier caliper, and the tumor volume was calculated. When the tumor grew to 100-200 mm³, the animals were randomly divided into groups, and intraperitoneally administrated according to the dosage shown in FIG. 34 and FIG. 35, with an administration volume of 0.2 mL/mouse (20g), biw, totally 6 times. The control group was set up and given the same dose of isotype control antibody.

During the experiment, the tumor volumes were measured twice a week, and the mice were weighed and recorded. The calculation formula of tumor volume (TV) was: TV=½× length×width². Tumor growth inhibition rate (TGI)=(1-tumor volume in experimental group/tumor volume in control group)×100%. According to statistical analysis, *p≤0.05 means effective, *** p≤0.001.

Figure 34:
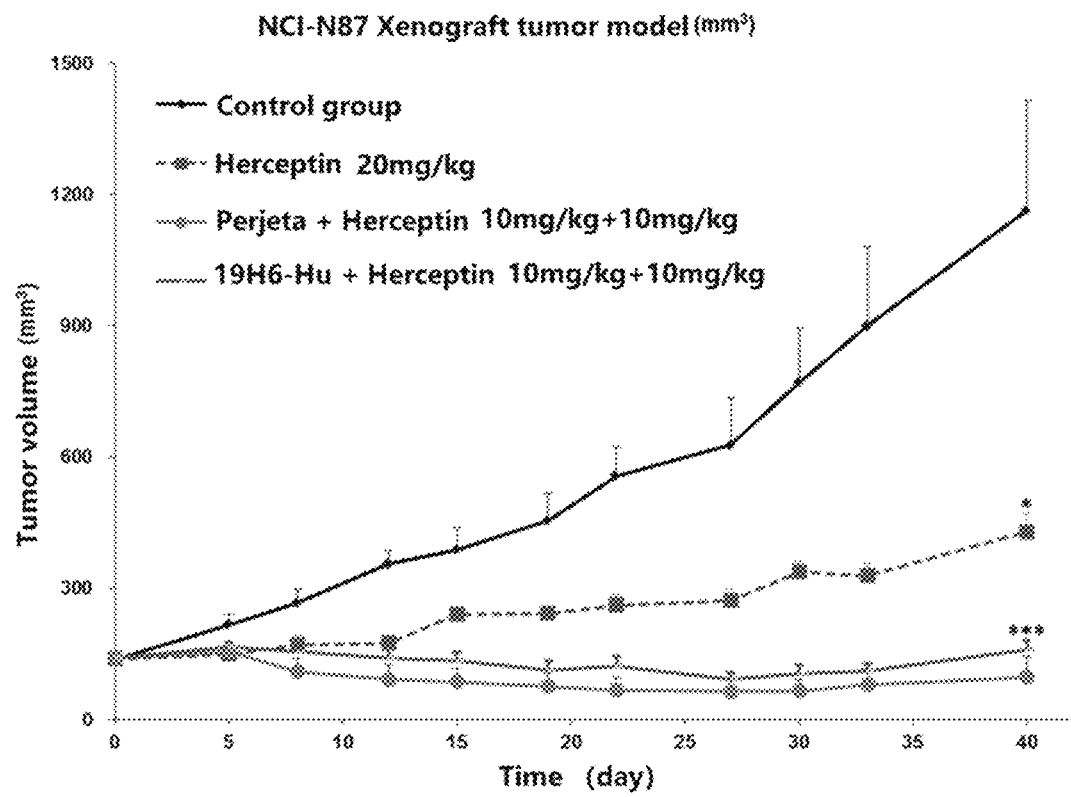
FIG. 34 shows the anti-tumor effect of the combination of 19H6-Hu and Herceptin on the NCI-N87 xenograft tumor model.

The results are shown in FIG. 34. NCI-N87 is a Herceptin sensitive model. Thus, when Herceptin was used as a single agent at a dose of 20 mg/kg, the TGI was 63.14%, p<0.05; but when Herceptin was combined with 19H6-Hu at a dose of 10 mg/kg+10 mg/kg, the anti-tumor effect was more significant, with a TGI of 86.31%, p<0.001, and its efficacy was comparable to the combination of Herceptin and Perjeta at the same dose, which has a TGI of 91.71%, p<0.001.

Figure 35:
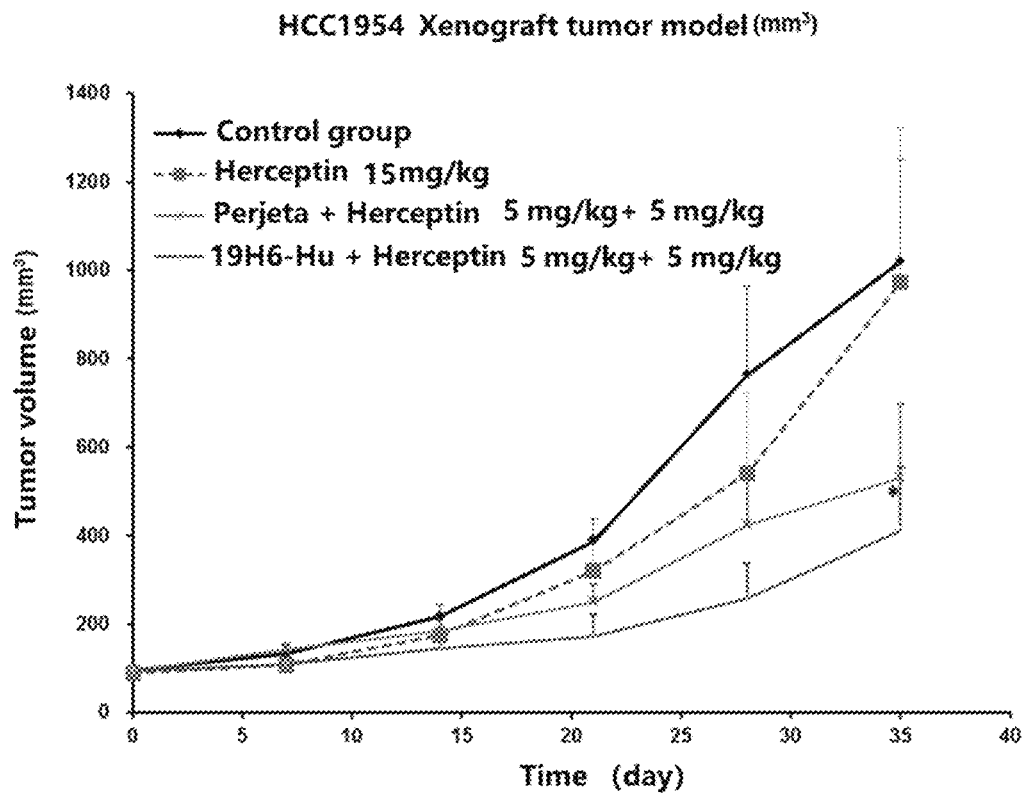
FIG. 35 shows the anti-tumor effect of the combination of 19H6-Hu and Herceptin on the HCC1954 xenograft tumor model.

The results are shown in FIG. 35. HCC1954 is a Herceptin insensitive model. Thus, Herceptin was almost ineffective when used as a single agent at a dose of 15 mg/kg, with a TGI of 4.67%, p>0.05; but when Herceptin was combined with 19H6-Hu at a dose of 5 mg/kg+5 mg/kg, the anti-tumor effect was relatively significant, with a TGI of 59.74%, $p<0.05$, and the efficacy was better than the combination of Herceptin and Perjeta at the same dose, which has a TGI of 48.05%.

During the experiment, the weight of the experimental animals did not decrease significantly, and no other side effects were observed. This indicates that when Herceptin is combined with 19H6-Hu, 19H6-Hu can significantly enhance the maximum anti-tumor effect of Herceptin.

What is claimed is:

1. An antibody or antigen-binding fragment thereof that binds to human HER2, comprising:
   (a) heavy chain complementarity determining regions HCDR1, HCDR2, and HCDR3, the HCDR1 having the amino acid sequence as shown in SEQ ID NO: 11, the HCDR2 having the amino acid sequence as shown in SEQ ID NO: 12, and the HCDR3 having the amino acid sequence as shown in SEQ ID NO: 13, and
   (b) light chain complementarity determining regions LCDR1, LCDR2, and LCDR3, the LCDR1 having the amino acid sequence as shown in SEQ ID NO: 14, the LCDR2 having the amino acid sequence as shown in SEQ ID NO: 15, and the LCDR3 having the amino acid sequence as shown in SEQ ID NO: 16.

2. The antibody or antigen-binding fragment thereof that binds to human HER2 according to claim 1, wherein the antibody is a monoclonal antibody, a polyclonal antibody, a murine antibody, a chimeric antibody or a humanized antibody.

3. The antibody or antigen-binding fragment thereof that binds to human HER2 according to claim 1, wherein the antigen-binding fragment comprises a Fab fragment, a F(ab')2 fragment, a Fv fragment, or a single chain antibody (scFv).

4. The antibody or antigen-binding fragment thereof that binds to human HER2 according to claim 1, wherein the antibody or antigen-binding fragment thereof that binds to human HER2 comprises a heavy chain variable region having the amino acid sequence as shown in SEQ ID NO: 3, and a light chain variable region having the amino acid sequence as shown in SEQ ID NO: 5; or the antibody or antigen-binding fragment thereof that binds to human HER2 comprises a heavy chain variable region having the amino acid sequence as shown in SEQ ID NO: 17, and a light chain variable region having the amino acid sequence as shown in SEQ ID NO: 19; or the antibody or antigen-binding fragment thereof that binds to human HER2 comprises a heavy chain variable region having the amino acid sequence as shown in SEQ ID NO: 21, and a light chain variable region having the amino acid sequence as shown in SEQ ID NO: 23.

5. The antibody or antigen-binding fragment thereof that binds to human HER2 according to claim 4, wherein the antibody or antigen-binding fragment thereof that binds to human HER2 comprises a heavy chain constant region having the amino acid sequence as shown in SEQ ID NO: 7, and a light chain constant region having the amino acid sequence as shown in SEQ ID NO: 9.

6. An isolated nucleic acid, wherein said nucleic acid encodes the antibody or antigen-binding fragment thereof that binds to human HER2 according to claim 1.

7. The nucleic acid according to claim 6, wherein said nucleic acid has the nucleotide sequence encoding the heavy chain variable region as shown in SEQ ID NO:4, and the nucleotide sequence encoding the light chain variable region as shown in SEQ ID NO: 6; or the nucleic acid has the nucleotide sequence encoding the heavy chain variable region as shown in SEQ ID NO: 18, and the nucleotide sequence encoding the light chain variable region as shown in SEQ ID NO: 20; or the nucleic acid has the nucleotide sequence encoding the heavy chain variable region as shown in SEQ ID NO: 22, and the nucleotide sequence encoding the light chain variable region as shown in SEQ ID NO: 24.

8. The nucleic acid according to claim 7, wherein said nucleic acid has the nucleotide sequence encoding the heavy chain constant region as shown in SEQ ID NO: 8, and the nucleotide sequence encoding the light chain constant region as shown in SEQ ID NO: 10.

9. An expression vector, wherein said expression vector comprises the nucleotide sequence according to claim 6.

10. A host cell, wherein said host cell comprises the expression vector according to claim 9.

11. A method of preparing the antibody or antigen-binding fragment thereof that binds to human HER2 as set forth in claim 1, wherein said method comprises the following steps:
 a) under expression conditions, cultivating a host cell that expresses the antibody or antigen-binding fragment thereof that binds to human HER2 thereby expressing the antibody or antigen-binding fragment thereof that binds to human HER2; and
 b) isolating and purifying the antibody or antigen-binding fragment thereof that binds to human HER2 expressed in step a).

12. A pharmaceutical composition, wherein said pharmaceutical composition comprises the antibody or antigen-binding fragment thereof that binds to human HER2 as set forth in claim 1, and a pharmaceutically acceptable carrier.

13. The pharmaceutical composition according to claim 12, wherein said pharmaceutical composition further comprises a second antibody or antigen-binding fragment thereof that binds to human HER2.

14. The pharmaceutical composition according to claim 13, wherein the second antibody or antigen-binding fragment thereof that binds to human HER2 comprises a heavy chain variable region and a light chain variable region, and the heavy chain variable region has the amino acid sequence as shown in SEQ ID NO: 25, the light chain variable region has the amino acid sequence as shown in SEQ ID NO: 26.

15. The pharmaceutical composition according to claim 14, wherein the second antibody or antigen-binding fragment thereof that binds to human HER2 is trastuzumab.

16. A method for the treatment of a HER2-overexpressing disease comprising administering to an individual in need thereof an antibody or antigen-binding fragment as set forth in claim 1 or the pharmaceutical composition according to claim 12.

17. The method of claim 16, wherein the HER2-overexpressing disease is cancer.

18. The method of claim 17, wherein the cancer comprises breast cancer, gastric cancer, or ovarian cancer.

* * * * *